(12) United States Patent
Llinas-Brunet et al.

(10) Patent No.: US 6,642,204 B2
(45) Date of Patent: Nov. 4, 2003

(54) HEPATITIS C INHIBITOR TRI-PEPTIDES

(75) Inventors: Montse Llinas-Brunet, Laval (CA); Vida J. Gorys, Laval (CA)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 10/353,589

(22) Filed: Jan. 29, 2003

(65) Prior Publication Data

US 2003/0187018 A1 Oct. 2, 2003

Related U.S. Application Data

(63) Continuation-in-part of application No. 10/321,218, filed on Dec. 17, 2002, now abandoned.

(51) Int. Cl.⁷ .................. A61K 38/06; A61K 31/4709; C07D 417/14
(52) U.S. Cl. .................. 514/18; 546/153; 514/312; 514/314
(58) Field of Search .................. 514/18, 312, 314; 546/153

(56) References Cited

U.S. PATENT DOCUMENTS

| | | |
|---|---|---|
| 6,159,938 A | 12/2000 | Gyorkos et al. |
| 6,187,905 B1 | 2/2001 | Hurst et al. |
| 6,323,180 B1 * | 11/2001 | Llinas-Brunet et al. ....... 514/18 |

FOREIGN PATENT DOCUMENTS

| | | |
|---|---|---|
| GB | 2 337 262 A | 11/1999 |
| JP | 10-298151 | 11/1998 |
| JP | 11-35478 | 2/1999 |
| JP | 11-127861 | 5/1999 |
| JP | 11-137252 | 5/1999 |
| JP | 11-292840 | 10/1999 |
| JP | 2001-103993 | 4/2001 |
| WO | WO 97/43310 A1 | 11/1997 |
| WO | WO 98/17679 A1 | 4/1998 |
| WO | WO 98/22496 A2 | 5/1998 |
| WO | WO 98/46597 A1 | 10/1998 |
| WO | WO 98/46630 A1 | 10/1998 |
| WO | WO 99/07733 A2 | 2/1999 |
| WO | WO 99/07734 A2 | 2/1999 |
| WO | WO 99/38888 A2 | 8/1999 |
| WO | WO 99/50230 A1 | 10/1999 |
| WO | WO 99/64442 A1 | 12/1999 |
| WO | WO 00/09543 A2 | 2/2000 |
| WO | WO 00/09543 A3 | 2/2000 |
| WO | WO 00/09558 A1 | 2/2000 |
| WO | WO 00/31129 A1 | 2/2000 |
| WO | WO 00/20400 A1 | 4/2000 |
| WO | WO 00/59929 A1 | 10/2000 |
| WO | WO 01/02424 A2 | 1/2001 |
| WO | WO 01/07407 A1 | 2/2001 |
| WO | WO 01/16357 A2 | 3/2001 |
| WO | WO 01/32691 A1 | 5/2001 |
| WO | WO 01/40262 A1 | 6/2001 |
| WO | WO 01/58929 A1 | 8/2001 |
| WO | WO 01/64678 A2 | 9/2001 |
| WO | WO 01/74768 A2 | 10/2001 |
| WO | WO 01/77113 A2 | 10/2001 |
| WO | WO 01/81325 A2 | 11/2001 |
| WO | WO 02/08187 A1 | 1/2002 |
| WO | WO 02/08198 A2 | 1/2002 |
| WO | WO 02/08244 A2 | 1/2002 |
| WO | WO 02/08251 A2 | 1/2002 |
| WO | WO 02/08256 A2 | 1/2002 |
| WO | WO 02/18369 A2 | 3/2002 |
| WO | WO 02/060926 A2 | 8/2002 |
| WO | WO 02/079234 A1 | 10/2002 |

OTHER PUBLICATIONS

Huang, et al; "Olefin Metathesis–Active Ruthenium Complexes Bearing a Nucleophilic Carbene Ligand", J. Am. Chem. Soc. 1999, 121, pp. 2674–2678.

Kingsbury, et al; "A Recyclable Ru–Based Metathesis Catalyst"; J. Am. Chem. Soc. 1999, 121, pp. 791–799.

(List continued on next page.)

*Primary Examiner*—Charanjit S. Aulakh
(74) *Attorney, Agent, or Firm*—Robert P. Raymond; Philip I. Datlow; Anthony P. Bottino

(57) ABSTRACT

Disclosed herein are compounds of formula (1):

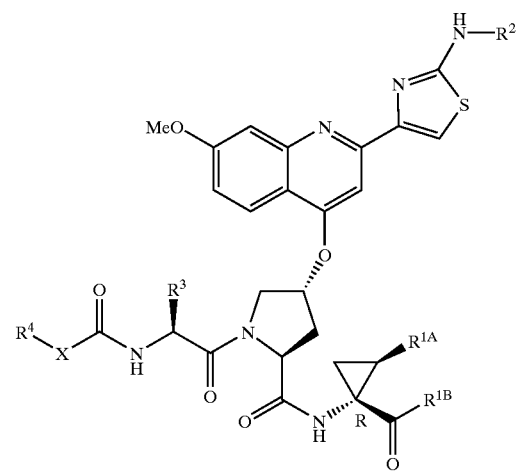

(1)

wherein $R^1$ is hydroxy or $NHSO_2R^{1A}$ wherein $R^{1A}$ is $(C_{1-8})$alkyl, $(C_{3-7})$cycloalkyl or $\{(C_{1-6})alkyl-(C_{3-7})cycloalkyl\}$, which are all optionally substituted from 1 to 3 times with halo, cyano, nitro, O—$(C_{1-6})$alkyl, amido, amino or phenyl, or $R^{1A}$ is $C_6$ or $C_{10}$ aryl which is optionally substituted from 1 to 3 times with halo, cyano, nitro, $(C_{1-6})$alkyl, O—$(C_{1-6})$ alkyl, amido, amino or phenyl; $R^2$ is $(C_{4-6})$cycloalkyl; $R^3$ is t-butyl or $(C_{5-6})$ cycloalkyl and $R^4$ is $(C_{4-6})$cycloalkyl; or a pharmaceutically acceptable salt thereof. The compounds are useful as inhibitors of HCV NS3 protease.

36 Claims, No Drawings

OTHER PUBLICATIONS

Krchnak, et al; "Polymer–Supported Mitsunobu Ether Formation and its Use in Combinatorial Chemistry"; Tetrahedron Ltrs., vol. 36, No. 35, pp. 6193–6916, 1995.

Lohmann, et al; "Replication of Subgenomic Hepatitis C Virus RNAs in a Hepatoma Cell Line"; Science, 1999, vol. 285, pp. 110–113.

Miller, et al; "Application of Ring–Closing Metathesis to the Synthesis of Rigidified Amino Acids and Peptides"; J. Am. Chem. Soc. 1996, 118, pp. 9606–9614.

Mitsunobu; "The Use of Diethyl Azodicarboxylate and Triphenylphosphine in Synthesis and Transformation of Natural Products"; Synthesis (Reviews), pp. 1–28.

Rano, et al; "Solid Phase Synthesis of Aryl Ethers Via the Mitsunobu Reaction"; Tetrahedron Ltrs., 1995, vol. 36, No. 22, pp. 3789–3792.

Still, et al; "Rapid Chromatographic Technique for Preparative Separations with Moderate Resolution"; J. Org. Chem. 1978, vol. 43, No. 14, pp. 2923–2925.

Derwent Abstract: AN 2001–435746 [47] (JP2001103993).
Derwent Abstract: AN 1999–040664 [04] (JP 10298151).
Derwent Abstract: AN 1999–350322 [30] (JP 11127861).
Derwent Abstract: AN 2000–018687 [02] (JP 11292840).
Derwent Abstract: AN 1999–186214 [16] (JP 11035478).
Derwent Abstract AN 1999–374374 [32] (JP 1113252).

* cited by examiner

SEQUENCE LISTING

<160> NUMBER OF SEQ ID NOS: 3

<210> SEQ ID NO 1
<211> LENGTH: 30
<212> TYPE: DNA
<213> ORGANISM: Artificial Sequence
<220> FEATURE:
<223> OTHER INFORMATION: Forward primer

<400> SEQUENCE: 1
acgcagaaag cgtctagcca tggcgttagt            30

<210> SEQ ID NO 2
<211> LENGTH: 30
<212> TYPE: DNA
<213> ORGANISM: Artificial Sequence
<220> FEATURE:
<223> OTHER INFORMATION: Reverse Primer

<400> SEQUENCE: 2
tcccggggca ctcgcaagca ccctatcagg            30

<210> SEQ ID NO 3
<211> LENGTH: 26
<212> TYPE: DNA
<213> ORGANISM: Artificial Sequence -continued

```
<220> FEATURE:
<223> OTHER INFORMATION: PUTR probe

<400> SEQUENCE: 3
tggtctgcgg aaccggtgag tacacc                                          26
```

HEPATITIS C INHIBITOR TRI-PEPTIDES

RELATED APPLICATIONS

This application is a Continuation-In-Part of U.S. application Ser. No. 10/321,218, filed on Dec. 17, 2002, now abandoned which application is herein incorporated by reference in its entirety.

FIELD OF THE INVENTION

The present invention relates to compounds, processes for their synthesis, compositions and methods for the treatment of hepatitis C virus (HCV) infection. In particular, the present invention provides novel peptide analogs, pharmaceutical compositions containing such analogs and methods for using these analogs in the treatment of HCV infection.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulins treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy. Pegylated forms of interferons such as PEG-Intron® and Pegasys® can apparently partially address these deleterious side-effects but antiviral drugs still remain the avenue of choice for oral treatment of HCV.

Therefore, a need exists for the development of effective antiviral agents for treatment of HCV infection that overcome the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, as yet poorly characterized, cleaves at the NS2-NS3 junction (henceforth referred to as NS2/3 protease); the second one is a serine protease contained within the N-terminal region of NS3 (NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protease with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

A general strategy for the development of antiviral agents is to inactivate virally encoded enzymes that are essential for the replication of the virus.

The following is a list of patent applications published in the last few years that disclose HCV NS3 protease inhibitor peptide analogs that are structurally different from the compounds of the present invention:

GB 2,337,262; JP10298151; JP 11126861; JP 11292840; JP 2001-103993; U.S. Pat. No. 6,159,938; U.S. Pat. No. 6,187,905; WO 97/43310; WO 98/17679; WO 98/22496; WO 98/46597; WO 98/46630; WO 99/38888; WO 99/50230; WO 99/64442; WO 99/07733; WO 99/07734; WO 00/09543; WO 00/09558; WO 00/20400; WO 00/59929; WO 00/31129; WO 01/02424; WO 01/07407; WO 01/16357; WO 01/32691; WO 01/40262; WO 01/58929; WO 01/64678; WO 01/74768; WO 01/77113; WO 01/81325; WO 02/08187; WO 02/08198; WO 02/08244; WO 02/08251; WO 02/08256; WO 02/18369; WO 02/60926 and WO 02/79234.

One advantage of the present invention is that it provides tripeptide compounds that are inhibitory to the NS3 protease, an enzyme essential for the replication of the hepatitis C virus. Furthermore, the compounds are able to inhibit HCV RNA replication in the replicon cell model.

A further advantage of one aspect of the present invention resides in the fact that the compounds specifically inhibit the NS3 protease and do not show significant inhibitory activity against other serine proteases such as human leukocyte elastase (HLE), porcine pancreatic elastase (PPE), or bovine pancreatic chymotrypsin, or cysteine proteases such as human liver cathepsin B (Cat B).

SUMMARY OF THE INVENTION

Included in the scope of the invention is a compound of formula (1):

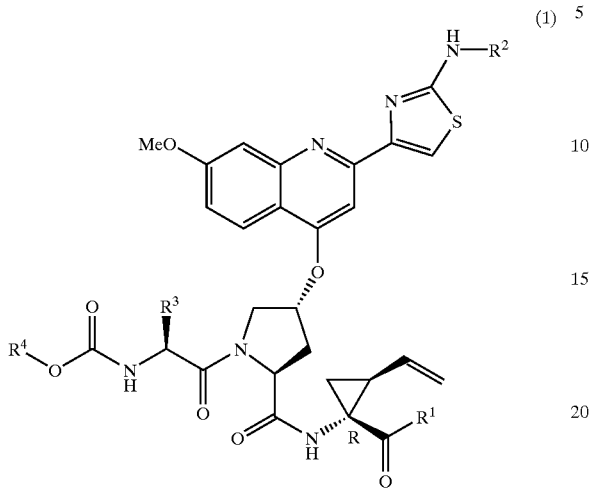

wherein $R^1$ is hydroxy or $NHSO_2R^{1A}$ wherein $R^{1A}$ is $(C_{1-8})$alkyl, $(C_{3-7})$cycloalkyl or $\{(C_{1-6})$alkyl-$(C_{3-7})$cycloalkyl$\}$, which are all optionally substituted from 1 to 3 times with halo, cyano, nitro, O—$(C_{1-6})$alkyl, amido, amino or phenyl, or $R^{1A}$ is $C_6$ or $C_{10}$ aryl which is optionally substituted from 1 to 3 times with halo, cyano, nitro, $(C_{1-6})$alkyl, O—$(C_{1-6})$alkyl, amido, amino or phenyl; $R^2$ is $(C_{4-6})$cycloalkyl; $R^3$ is t-butyl or $(C_{5-6})$ cycloalkyl and $R^4$ is $(C_{4-6})$cycloalkyl; or a pharmaceutically acceptable salt thereof.

Included within the scope of this invention is a pharmaceutical composition comprising an anti-hepatitis C virally effective amount of a compound of formula I, or a therapeutically acceptable salt thereof, in admixture with a pharmaceutically acceptable carrier medium or auxiliary agent.

According to one embodiment, the pharmaceutical composition of this invention further comprises interferon (pegylated or not), or ribavirin, or one or more other anti-HCV agent, or any combination of the above.

Another important aspect of the invention involves a method of treating a hepatitis C viral infection in a mammal by administering to the mammal an anti-hepatitis C virally effective amount of a compound of formula I, a pharmaceutically acceptable salt thereof, or a composition as described above, alone or in combination with one or more of: interferon (pegylated or not), or ribavirin, or one or more other anti-HCV agents, administered together or separately, e.g., prior to, concurrently with or following the administration of the compound of formula I or pharmaceutically acceptable salt thereof.

Another important aspect of the invention involves a method of preventing a hepatitis C viral infection in a mammal by administering to the mammal an anti-hepatitis C virally effective amount of a compound of formula I, a pharmaceutically acceptable salt thereof, or a composition as described above, alone or in combination with one ore more of: interferon (pegylated or not), or ribavirin, or one or more other anti-HCV agents, all of which administered together or separately, e.g., prior to, concurrently with or following the administration of the compound of formula I or pharmaceutically acceptable salt thereof.

Also within the scope of this invention is the use of a compound of formula I, as described herein, for the manufacture of a medicament for the treatment or prevention of hepatitis C viral infection.

The present description refers to a number of documents, the content of which is herein incorporated by reference.

DETAILED DESCRIPTION OF PREFERRED EMBODIMENTS

Definitions

As used herein, the following definitions apply unless otherwise noted:

With reference to the instances where (R) or (S) is used to designate the absolute configuration of a substituent or asymmetric centre of a compound of formula 1, the designation is done in the context of the whole compound and not in the context of the substituent or asymmetric centre alone.

The designation "P1, P2, and P3" as used herein refer to the position of the amino acid residues starting from the C-terminus end of the peptide analogs and extending towards the N-terminus (i.e. P1 refers to position 1 from the C-terminus, P2: second position from the C-terminus, etc.) (see Berger A. & Schechter I., Transactions of the Royal Society London series B257, 249–264 (1970)).

As used herein the term "vinyl-ACCA" refers to a compound of formula:

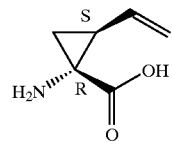

namely, (1R,2S)1-amino-2-ethenylcyclopropylcarboxylic acid. The term "$(C_{1-8})$alkyl" as used herein, either alone or in combination with another substitutent, means acyclic straight or branched alkyl substituents containing for 1 to 8 carbon atoms and includes, for example, methyl, ethyl, 2-methylhexyl, 1,1-dimethylhexyl (or t-butyl) and octyl.

The term "$(C_{3-7})$cycloalkyl" as used herein, either alone or in combination with another substituent, means a cycloalkyl substituent containing from 3 to 7 carbon atoms and includes cyclopropyl, cyclobutyl, cyclopentyl, cyclohexyl and cycloheptyl.

The term "$\{(C_{1-6})$alkyl-$(C_{3-6})$cycloalkyl$\}$" as used herein means a cycloalkyl radical containing from 3 to 6 carbon atoms directly linked to an alkylene radical containing 1 to 6 carbon atoms; for example, cyclopropylmethyl, cyclopentylethyl, cyclohexylmethyl, and cyclohexylethyl. In the instance where $R^{1A}$ is a $\{(C_{1-6})$alkyl-$(C_{3-6})$cycloalkyl$\}$, this group is attached to the $SO_2$ group via the $(C_{1-6})$alkyl (i.e. the alkylene portion).

The term "$C_6$ or $C_{10}$ aryl" as used herein, either alone or in combination with another radical, means either an aromatic monocyclic group containing 6 carbon atoms or an aromatic bicyclic group containing 10 carbon atoms. For example, aryl includes phenyl, 1-naphthyl or 2-naphthyl.

The term "O—$(C_{1-6})$ alkyl" as used herein, either alone or in combination with another radical, means the radical —O—$(C_{1-6})$alkyl wherein alkyl is as defined above containing up to six carbon atoms, and includes methoxy, ethoxy, propoxy, 1-methylethoxy, butoxy and 1,1-dimethylethoxy. The latter radical is known commonly as tert-butoxy.

The term "halo" as used herein means a halogen substituent selected from bromo, chloro, fluoro or iodo.

The term "pharmaceutically acceptable salt" means a salt of a compound of formula (1) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1–19, which is hereby incorporated by reference in its entirety.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Antiviral agents include, for example, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals).

The term other anti-HCV agent as used herein means those agents that are effective for diminishing or preventing the progression of hepatitis C related symptoms of disease. Such agents can be selected from: antiviral agents, immunomodulatory agents, inhibitors of HCV NS3 protease, inhibitors of HCV polymerase or inhibitors of another target in the HCV life cycle.

The term "immunomodulatory agent" as used herein means those agents (compounds or biologicals) that are effective to enhance or potentiate the immune system response in a mammal. Immunomodulatory agents include, for example, class I interferons (such as α-, β- and omega interferons, tau-interferons, consensus interferons and asialo-interferons), class II interferons (such as γ-interferons) and pegylated interferons.

The term "inhibitor of HCV NS3 protease" as used herein means an agent (compound or biological) that is effective to inhibit the function of HCV NS3 protease in a mammal. Inhibitors of HCV NS3 protease include, for example, those compounds described in WO 99/07733, WO 99/07734, WO 00/09558, WO 00/09543, WO 00/59929 or WO 02/060926, and the Vertex/Eli Lilly pre-development candidate identified as VX-950 or LY-570310. Particularly, compounds #2, 3, 5, 6, 8, 10, 11, 18, 19, 29, 30, 31, 32, 33, 37, 38, 55, 59, 71, 91, 103, 104, 105, 112, 113, 114, 115, 116, 120, 122, 123, 124, 125, 126 and 127 disclosed in the table of pages 224–226 in WO 02/060926, can be used in combination with the compounds of the present invention.

The term "inhibitor of HCV polymerase" as used herein means an agent (compound or biological) that is effective to inhibit the function of an HCV polymerase in a mammal. This includes, for example, inhibitors of HCV NS5B polymerase. Inhibitors of HCV polymerase include non-nucleosides, for example, those compounds described in:

U.S. application Ser. No. 10/198,680, herein incorporated by reference in its entirety, which corresponds to PCT/CA02/01127, both filed Jul. 18, 2002 (Boehringer Ingelheim), U.S. application Ser. No. 10/198,384, herein incorporated by reference in its entirety, which corresponds to PCT/CA02/01128, both filed Jul. 18, 2002 (Boehringer Ingelheim), U.S. application Ser. No. 10/198,259, herein incorporated by reference in its entirety, which corresponds to PCT/CA02/01129, both filed Jul. 18, 2002 (Boehringer Ingelheim), WO 02/100846 A1 and WO 02/100851 A2 (both Shire), WO 01/85172 A1 and WO 02/098424 A1 (both GSK), WO 00/06529 and WO 02/06246 A1 (both Merck), WO 01/47883 and WO 03/000254 (both Japan Tobacco) and EP 1 256 628 A2 (Agouron).

Furthermore other inhibitors of HCV polymerase also include nucleoside analogs, for example, those compounds described in:

WO 01/90121 A2 (Idenix),

WO 02/069903 A2 (Biocryst Pharmaceuticals Inc.), and

WO 02/057287 A2 and WO 02/057425 A2 (both Merck/Isis).

Specific examples of inhibitors of an HCV polymerase, include JTK-002, JTK-003 and JTK-109 (Japan Tobacco).

The term "inhibitor of another target in the HCV life cycle" as used herein means an agent (compound or biological) that is effective to inhibit the formation and/or replication of HCV in a mammal other than by inhibiting the function of the HCV NS3 protease or HCV polymerase. This includes agents that interfere with either host or HCV viral mechanisms necessary for the formation and/or replication of HCV in a mammal. Inhibitors of another target in the HCV life cycle include, for example, agents that inhibit a target selected from a helicase, an HCV NS2/3 protease and an inhibitor of internal ribosomal entry site (IRES). Specific examples of inhibitors of another target in the HCV life cycle include JTK-003/002 (Japan Tobacco) and ISIS-14803 (ISIS Pharmaceuticals).

The term "HIV inhibitor" as used herein means an agents (compound or biological) that is effective to inhibit the formation and/or replication of HIV in a mammal. This includes agents that interfere with either host or viral mechanisms necessary for the formation and/or replication of HIV in a mammal. HIV inhibitors include, for example, nucleosidic inhibitors, non-nucleosidic inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type I. This includes both naturally and synthetically produced class I interferons. Examples of class I interferons include α-, β, omega interferons, tau-interferons, consensus interferons, asialo-interferons.

The term "class II interferon" as used herein means an interferon selected from a group of interferons that all bind to receptor type II. Examples of class II interferons include γ-interferons.

The pharmaceutical compositions of the invention may contain one or more additional active agents selected, for example, from antiviral agents, immunomodulatory agents, other inhibitors of HCV NS3 protease, inhibitors of HCV polymerase or inhibitors of another target in the HCV life cycle, HIV inhibitors, HAV inhibitors and HBV inhibitors. Examples of such agents are provided in the Definitions section above.

Specific preferred examples of some of these agents are listed below:

antiviral agents: ribavirin and amantadine;

immunomodulatory agents: class I interferons, class II interferons and pegylated interferons;

inhibitor of another target in the HCV life cycle that inhibits a target selected from: NS3 helicase, HCV NS2/3 protease or internal ribosome entry site (IRES);

HIV inhibitors: nucleosidic inhibitors, non-nucleosidic inhibitors, protease inhibitors, fusion inhibitors and integrase inhibitors; or HBV inhibitors: agents that inhibit HBV viral DNA polymerase or is an HBV vaccine.

As discussed above, combination therapy is contemplated wherein a compound of formula (1), or a pharmaceutically acceptable salt thereof, is co-administered with at least one additional agent selected from: an antiviral agent, an immunomodulatory agent, another inhibitor of HCV NS3 protease, inhibitor of HCV polymerase, an inhibitor of another target in the HCV life cycle, an HIV inhibitor, an HAV inhibitor and an HBV inhibitor. Examples of such agents are provided in the Definitions section above. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of wherein a compound of formula (1), or a pharmaceutically acceptable salt thereof.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood.

Preferred Embodiments

Preferably, compounds of formula 1 as defined above wherein $R^1$ is hydroxy, $NHSO_2Me$, $NHSO_2$cyclopropyl or $NHSO_2Ph$. More preferably, $R^1$ is $NHSO_2$-cyclopropyl or $NHSO_2Ph$. Alternatively, most preferably, $R^1$ is hydroxy.

Preferably, compounds of formula 1 as defined above wherein $R^2$ is cyclopentyl or cyclohexyl. Most preferably, $R^2$ is cyclopentyl.

Preferably, $R^3$ is t-butyl or cyclohexyl. Most preferably, $R^3$ is t-butyl.

Preferably, compounds of formula 1 as defined above wherein $R^4$ is cyclobutyl or cyclopentyl. Most preferably, $R^4$ is cyclopentyl.

More preferably, a compound of formula 1 as defined above wherein $R^1$ is hydroxy, $R^2$ and $R^4$ each is cyclopentyl and $R^3$ is t-butyl.

More preferably, a compound of formula 1 wherein $R^1$ is hydroxy, $R^2$ is cyclobutyl, $R^3$ is t-butyl and $R^4$ is cyclopentyl.

More preferably, a compound of formula 1 wherein $R^1$ is hydroxy, $R^2$ is cyclohexyl, $R^3$ is t-butyl and $R^4$ is cyclopentyl.

More preferably $R^1$ is $NHSO_2Ph$, $R^2$ and $R^4$ each is cyclopentyl and $R^3$ t-butyl.

More preferably, a compound of formula 1 wherein $R^1$ is hydroxy, $R^2$ is cyclopentyl, $R^3$ is t-butyl and $R^4$ is cyclobutyl.

More preferably, a compound of formula 1 wherein $R^1$ is hydroxy, $R^2$ is cyclopentyl, $R^3$ is t-butyl and $R^4$ is cyclohexyl.

More preferably, a compound of formula 1 wherein $R^1$ is hydroxy, $R^2$ and $R^4$ each is cyclopentyl and $R^3$ is cyclohexyl.

More preferably, a compound of formula 1 wherein $R^1$ is hydroxy, $R^2$, $R^3$ and $R^4$ each is cyclopentyl.

According to an alternate embodiment, the pharmaceutical composition of this invention may additionally comprise another anti-HCV agent. Examples of anti-HCV agents include, α-(alpha), β-(beta), δ-(delta), γ-(gamma) or ω-(omega) interferon, ribavirin and amantadine.

According to another alternate embodiment, the pharmaceutical composition of this invention may additionally comprise another inhibitor of HCV NS3 protease.

According to another alternate embodiment, the pharmaceutical composition of this invention may additionally comprise an inhibitor of HCV polymerase.

According to yet another alternate embodiment, the pharmaceutical composition of this invention may additionally comprise an inhibitor of other targets in the HCV life cycle, including but not limited to, helicase, NS2/3 protease or internal ribosome entry site (IRES).

The pharmaceutical composition of this invention may be administered orally, parenterally or via an implanted reservoir. Oral administration or administration by injection is preferred. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, $19^{th}$ Ed. Mack Publishing Company, Easton, Pa., (1995).

Dosage levels of between about 0.01 and about 100 mg/kg body weight per day, preferably between about 0.1 and about 50 mg/kg body weight per day of the protease inhibitor compound described herein are useful in a monotherapy for the prevention and treatment of HCV mediated disease. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the composition of this invention comprise a combination of a compound of formula 1 and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit HCV NS3 protease or to treat or prevent HCV virus infection.

Such treatment may also be achieved using a compound of this invention in combination with agents which include, but are not limited to: α-, β-, δ-, ω-, or γ-interferon, ribavirin, amantadine; other inhibitors of HCV NS3 protease; inhibitors of HCV polymerase; inhibitors of other targets in the HCV life cycle, which include but not limited to, helicase, NS2/3 protease, or internal ribosome entry site (IRES); or combinations thereof. The additional agents may be combined with compounds of this invention to create a single dosage form. Alternatively these additional agents may be separately administered to a mammal as part of a multiple dosage form.

Accordingly, another embodiment of this invention provides a method of inhibiting HCV NS3 protease activity in a mammal by administering a compound of the formula 1.

In a preferred embodiment, this method is useful in decreasing the NS3 protease activity of the hepatitis C virus infecting a mammal.

If the pharmaceutical composition comprises only a compound of this invention as the active component, such method may additionally comprise the step of administering to said mammal an agent selected from an immunomodulatory agent, an antiviral agent, a HCV NS3 protease inhibitor, an inhibitor of HCV polymerase or an inhibitor of other targets in the HCV life cycle such as helicase, NS2/3 protease or IRES. Such additional agent may be administered to the mammal prior to, concurrently with, or following the administration of the composition of this invention.

A compound of formula 1 set forth herein may also be used as a laboratory reagent. A compound of this invention may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

A compound of formula 1 set forth herein may also be used as a research reagent. A compound of formula 1 may also be used as positive control to validate surrogate cell-based assays or in vitro or in vivo viral replication assays.

Further details of the invention are illustrated in the following examples which are understood to be non-limiting with respect to the appended claims.

Methodology

In general, the compounds of formula 1, and intermediates therefore, are prepared by known methods using reaction conditions which are known to be suitable for the reactants. Several such methods are disclosed in WO 00/09543, WO 00/09558 and U.S. Pat. No. 6,323,180, incorporated herein by reference.

Compounds of formula I wherein $R^1$ is $NHSO_2R^{1A}$ as defined herein are prepared by coupling the corresponding acid of formula I (i.e. $R^1$ is hydroxy) with an appropriate sulfonamide of formula $R^{1A}SO_2NH_2$ in the presence of a coupling agent under standard conditions. Although several commonly used coupling agents can be employed, TBTU and HATU have been found to be practical. The sulfonamides are available commercially or can be prepared by known methods.

The following schemes illustrate two convenient processes using known methods for preparing the compounds of formula 1 when $R^1$ is OH.

Scheme 1:

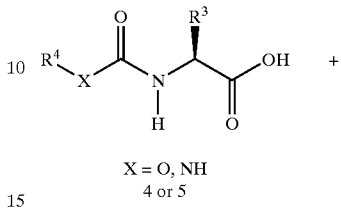

X = O, NH
4 or 5

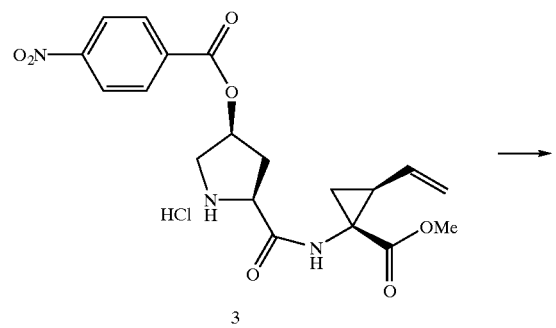

3

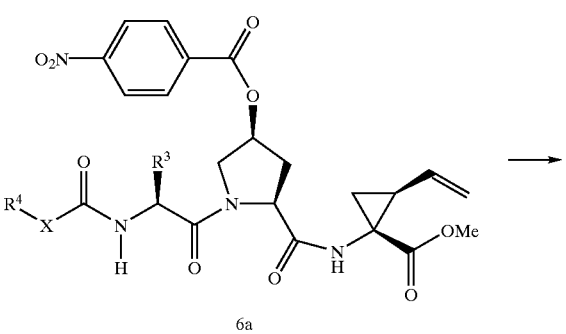

6a

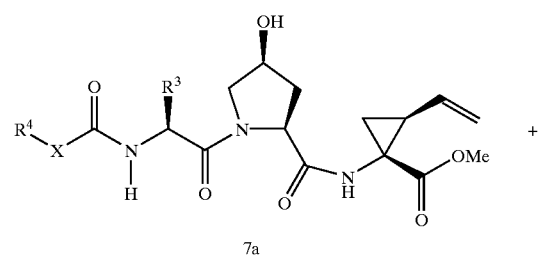

7a

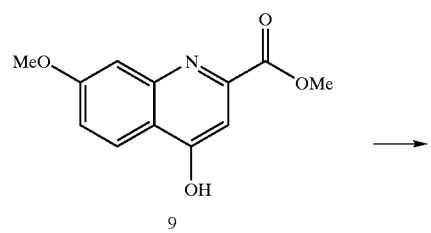

9

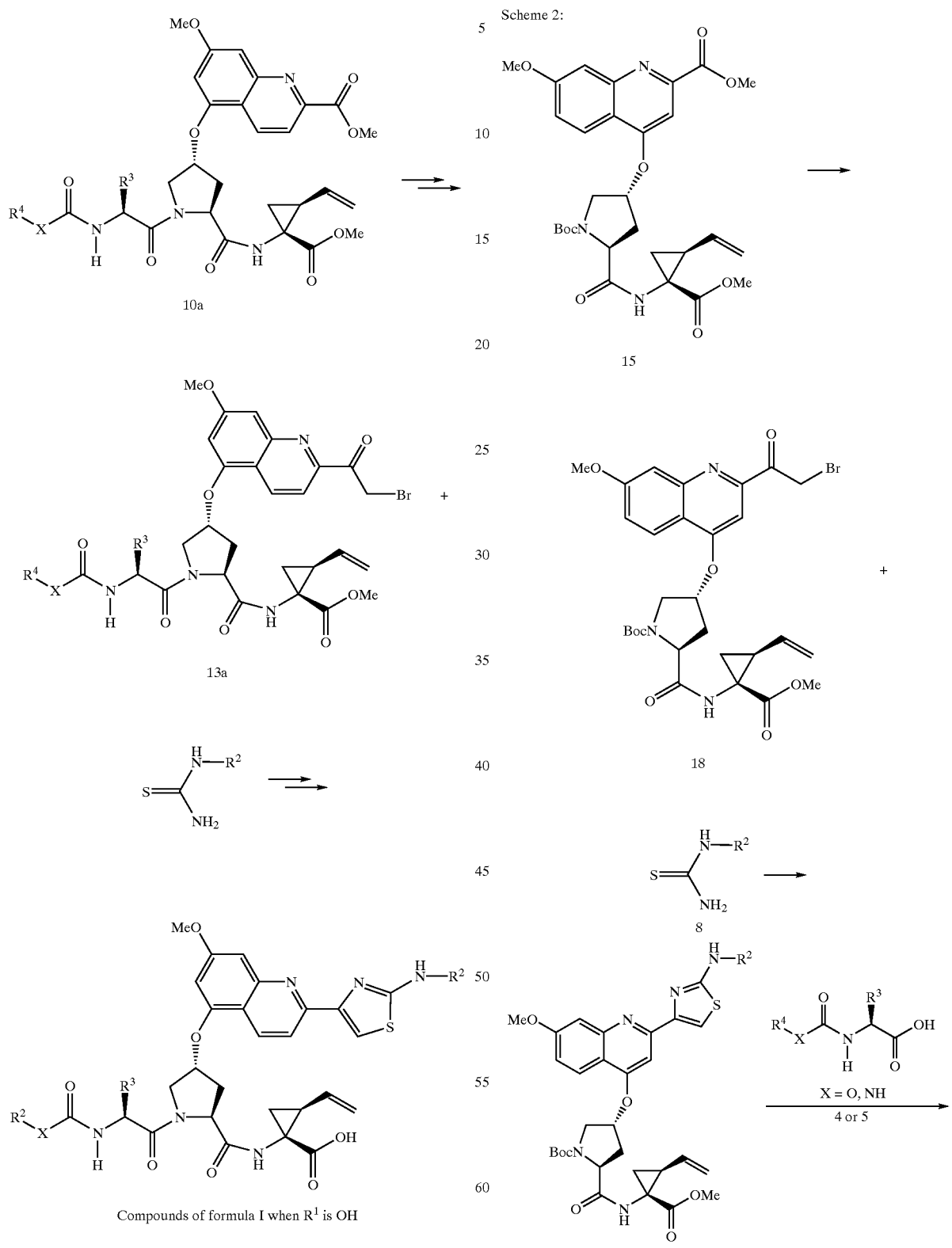

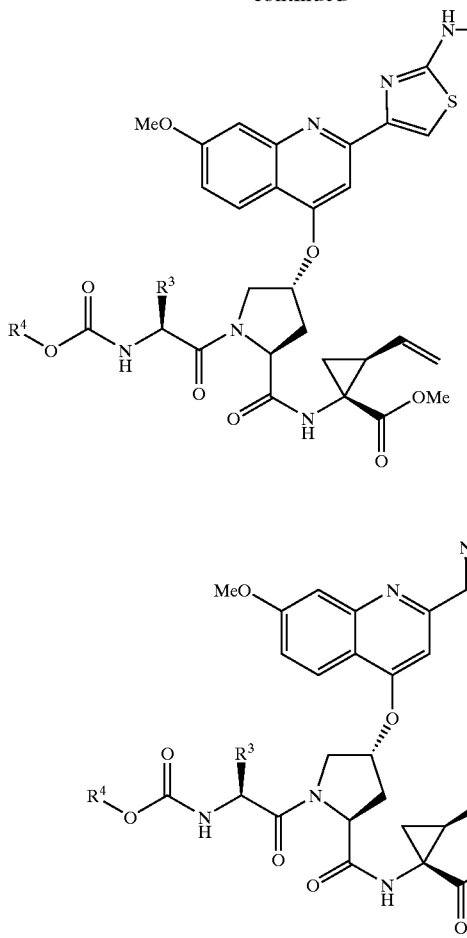

Compounds of formula I when R¹ is OH

EXAMPLES

Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million. Flash chromatography was carried out on silica gel (SiO₂) according to Still's flash chromatography technique (W. C. Still et al., J. Org. Chem., (1978), 43, 2923).

Abbreviations used in the examples include:

DBU: 1,8-diazabicyclo[5.4.0]undec-7-ene; DCM: dichloromethane; DIAD: diisopropylazodicarboxylate; DIEA: diisopropylethylamine; DIPEA: diisopropylethyl amine; DMF: N,N-dimethylformamide; DMAP: 4-(dimethylamino) pyridine; EtOAc: ethyl acetate; HATU: [O-7-azabenzotriazol-1-yl)-1,1,3,3-tetramethyluronium hexafluorophosphate]; HPLC: high performance liquid chromatography; MS: mass spectrometry (MALDI-TOF: Matrix Assisted Laser Disorption Ionization-Time of Flight, FAB: Fast Atom Bombardment); Me: methyl; MeOH: methanol; Ph: phenyl; R.T.: room temperature (18 to 22°); tert-butyl or t-butyl: 1,1-dimethylethyl; Tbg: tert-butyl glycine: tert-leucine; TBTU: 2-(1H-benzotriazole-1-yl)-1,1,3,3-tetramethyluronium tetrafluoroborate; TFA: trifluoroacetic acid; and THF: tetrahydrofuran.

Synthesis of Compounds of Formula (I)

The dipeptide intermediate 15 (Scheme 2) and 2-carbomethoxy-4-hydroxy-7-methoxyquinoline 9 (Scheme 1) were synthesized according to the methods described in WO 00/09543.

Synthesis of Dipeptide 1

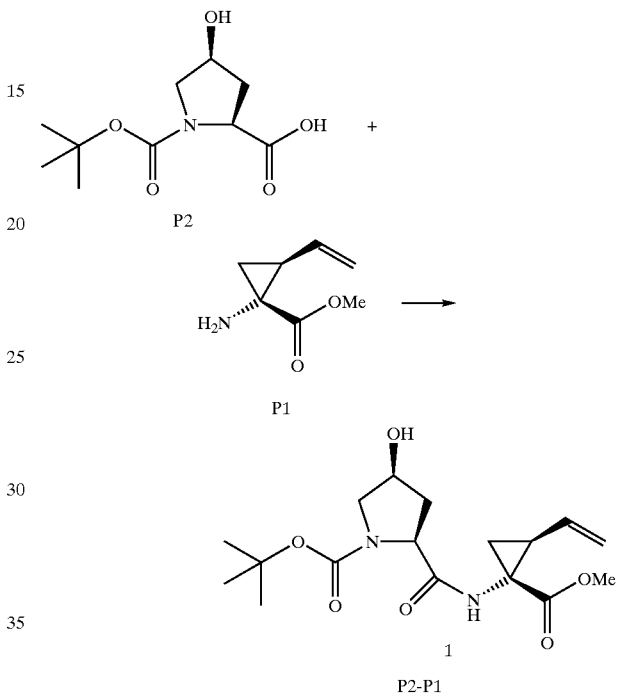

A mixture of Boc-hydroxyproline (50.0 g, 216 mmol), vinyl-ACCA methyl ester (42.25 g, 238 mmol, 1.1 equiv.), TBTU (76.36 g, 238 mmol, 1.1 equiv.) and DIPEA (113 mL, 649 mmol, 3 equiv.) in DMF (800 mL) was stirred at R.T. under a nitrogen atmosphere. After 3.5 h, the solvent was evaporated and the residue extracted with EtOAc. The extract was washed with hydrochloric acid (10%), saturated sodium bicarbonate and brine. The organic phase was then dried over magnesium sulfate, filtered and evaporated to afford an oil. After drying overnight under high vacuum, dipeptide 1 was obtained as a yellow foam (72.0 g, 94%, purity >95% by HPLC).

Preparation of Dipeptide 3

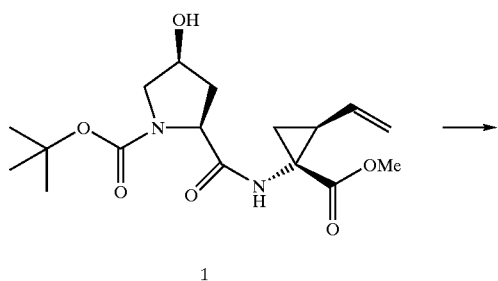

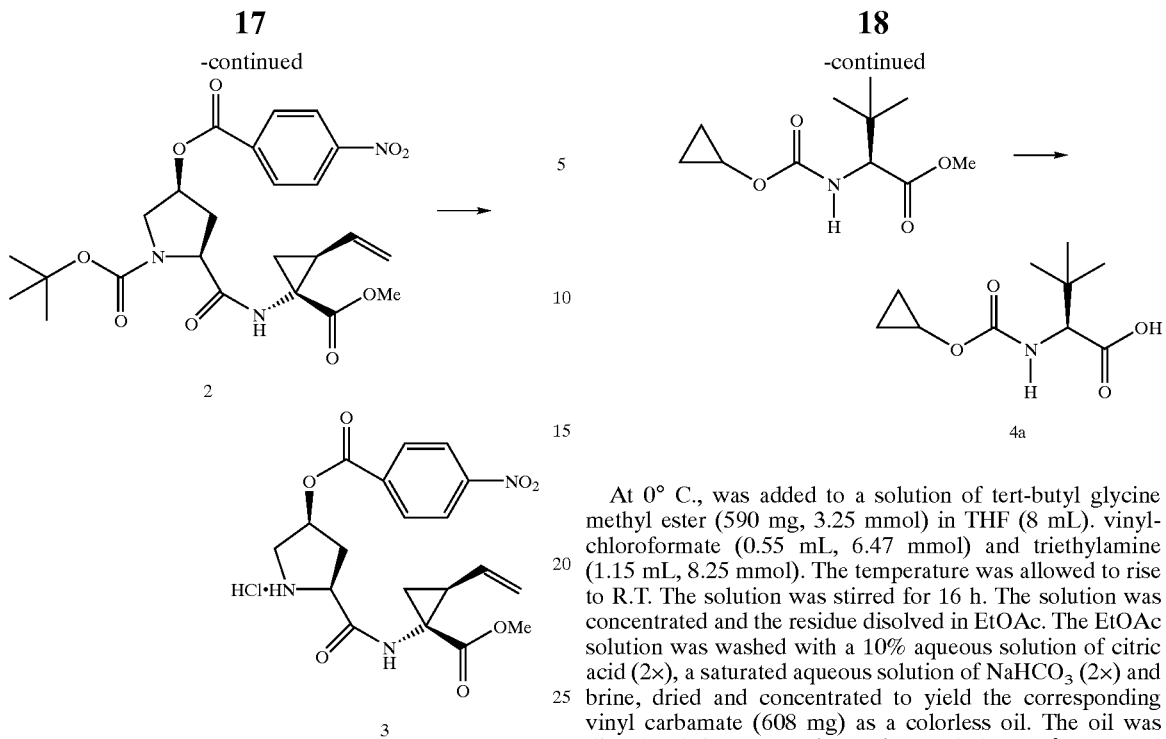

Dipeptide 1 (72.0 g, 203 mmol), triphenylphosphine (63.94 g, 243.8 mmol, 1.2 equiv.) and 4-nitrobenzoic acid (41.08 g, 245.8 mmol, 1.2 equiv) were dissolved in dry THF (1.4L) The stirred solution was cooled to 0° C. under a nitrogen atmosphere. Diethyl azodicarboxylate (38.4 mL, 244 mmol, 1.2 equiv.) was then added dropwise over 45 min and the reaction allowed to warm to R.T. After 4 h, the solvent was evaporated. The residue was divided into four portions. Each of these was purified by chromatography over fine silica gel (10–40 µm mesh, column diameter 12 cm, column length 16 cm) using a gradient of 2:1 hexane/EtOAc to 1:1 hexane/EtOAc to pure EtOAc. In this manner, the Boc-dipeptide ester 2 was obtained as an amorphous white solid after evaporation of the solvents and drying of the residues under high vacuum at 70° C. for 1 h (108.1 g, quantitative-105%). A solution of 4N hydrogen chloride in dioxane was added to the Boc-dipeptide ester 2 (108 g, 243 mmol) resulting in a colorless solution. The solution was stirred at R.T. for 1 h. The solvent was evaporated and the residue placed under high vacuum for 3 h affording the hydrochloride salt of compound 3 as an amorphous solid. The solid was used as such.

Synthesis of Carbamates 4

Preparation of Carbamate 4a:

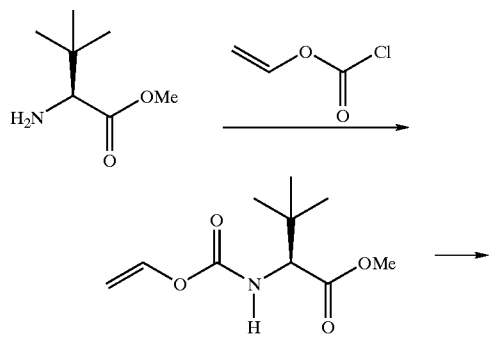

At 0° C., was added to a solution of tert-butyl glycine methyl ester (590 mg, 3.25 mmol) in THF (8 mL). vinyl-chloroformate (0.55 mL, 6.47 mmol) and triethylamine (1.15 mL, 8.25 mmol). The temperature was allowed to rise to R.T. The solution was stirred for 16 h. The solution was concentrated and the residue disolved in EtOAc. The EtOAc solution was washed with a 10% aqueous solution of citric acid (2×), a saturated aqueous solution of $NaHCO_3$ (2×) and brine, dried and concentrated to yield the corresponding vinyl carbamate (608 mg) as a colorless oil. The oil was dissolved in DCM (4 mL), cooled at 0° C., and diiodomethane (0.15 mL, 1.86 mmol) and diethylzinc (95 µL, 0.93 mmol) were added. A white solid appeared at first but dissolved with time (~1 h). The suspension/solution was stirred at R.T. for 5 h. A saturated solution of ammonium chloride was added and the solution extracted with EtOAc (2×). The organic extract was dried ($MgSO_4$) and concentrated. The residue was purified by flash column chromatography. Elution with hexane:EtOAc 95:5 gave the corresponding methyl ester as a colorless oil (96 mg, 90% yield).

A solution the methyl ester (93 mg; 0.41 mmol) in THF (5 mL), MeOH (1 mL) and an aqueous solution of LiOH (45 mg; 1.81 mmol) in water (2 mL) was stirred for 4 h. The solution is dilute with water and extracted with EtOAc (2×). The aqueous solution was acidified by the addition of 1N HCl, and the acidic solution was extracted with EtOAc (2×). The combined organic extracts were dried (MgSO4), filtered and evaporated to obtain the desired carbamate 4a as a white solid (53 mg; 60% yield).

Preparation of Carbamate 4b

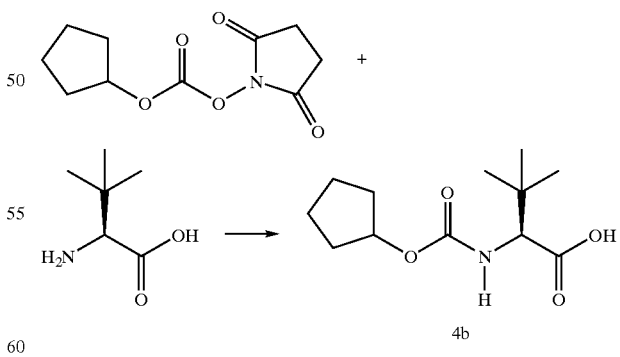

THF (350 mL) was added to a flask containing carbonic acid cyclopentyl ester 2,5-dioxo-pyrrolidin-1-yl ester (9.00 g; 39.6 mmol) and tert-butyl glycine (6.24 g; 47.5 mmol) resulting in a suspension. Distilled water (100 mL) was added with vigorous stirring. A small amount of solid remained undissolved. Triethylamine (16.6 mL; 119 mmol)

was then added resulting in a homogenous solution which was stirred at R.T. After 2.5 h, the THF was evaporated and the aqueous residue diluted with water (100 mL). The reaction was rendered basic by the addition of 1 N NaOH (25 mL-final pH>10). The solution was washed with EtOAc (2×200 mL) and the aqueous phase acidified with 1 N HCl (ca. 70 mL-final pH<2). The turbid solution was extracted with EtOAc (200+50 mL). The extract was dried (MgSO$_4$) and evaporated to give carbamate 4b as a white solid (8.68 g).

Preparation of Other Carbamates

Using the procedure described above and using appropriate combinations of tert-butyl glycine, cyclopentyl glycine, or cyclohexyl glycine and carbonic acid cyclobutyl, cyclopentyl, or cyclohexyl ester 2,5-dioxo-pyrrolidin-1-yl ester, carbamates of the following formulas were prepared:

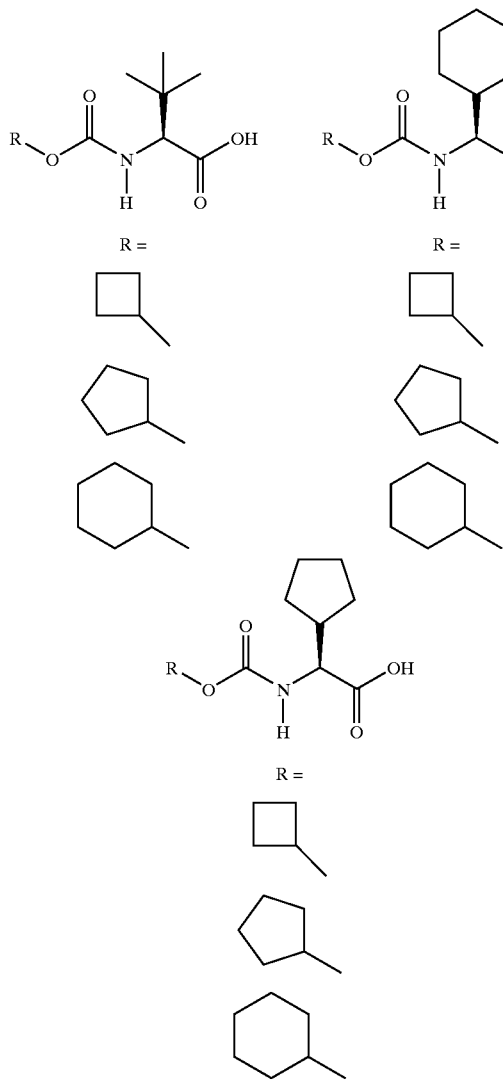

Preparation of Ureas 5

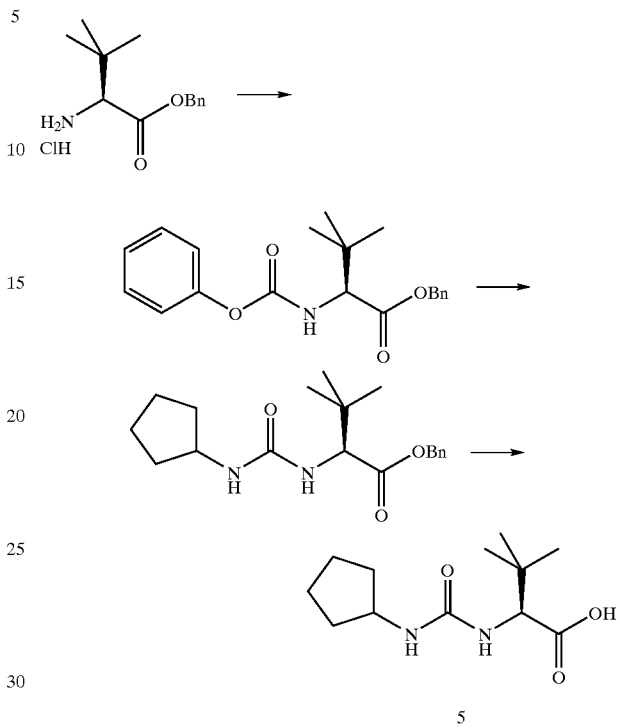

5

A solution of tert-butyl glycine benzyl ester hydrochloride salt (2.55 g; 9.89 mmol) in THF (20 mL) and pyridine (2.0 mL; 24.73 mmol) was cooled to 0° C. Phenyl chloroformate (1.30 mL; 10.19 mmol) was added dropwise to the cooled solution. The resulting suspension was stirred for 5 min at 0° C., then at R.T. for 1.5 h. The reaction mixture was diluted with EtOAc, washed with 10% citric acid (2×) water (2×) saturated NaHCO$_3$ (2×), water (2×) and brine (1×), dried (MgSO4), filtered and evaporated to gain the crude compound as a nearly colorless oil (3.73 g; >100%; assume 9.89 mmol). The crude product (1.01 g; 2.97 mmol) was dissolved in DMSO (6.5 mL) and cyclopentylamine was added dropwise. The reaction mixture was stirred at R.T. for 45 min. The reaction mixture was diluted with EtOAc. The organic phase was washed with washed with 10% citric acid (2×) water (2×) saturated NaHCO$_3$ (2×), water (2×) and brine (1×), dried (MgSO4), filtered and evaporated to give the crude cyclopentyl urea-Tbg-OBn product as a nearly colorless oil. The crude material was purified by flash column chromatography with silica using hexane:EtOAc 9:1 to remove the less polar impurities and 7:3 to elute the purified product as a thick colourless oil (936 mg; 95%). The ester benzyl ester product (936 mg; 2.82 mmol) was deprotected under a hydrogen filled balloon at R.T. in absolute ethanol (15 mL) solution by stirring the solution with 10% Pd/C (93.6 mg) for 5.5 h. The reaction mixture was filtered through a 0.45 micron filter and evaporated to dryness to provide urea 5 as a white solid (668.8 mg; 98%)

$^1$H NMR (400 MHz, DMSO-d$_6$): δ 12.39 (s, 1H), 6.09 (d, J=7.4 Hz, 1H), 5.93 (d, J=9.4 Hz, 1H), 3.90 (d, J=9.4 Hz, 1H), 3.87–3.77 (m, 1H), 1.84–1.72 (m, 2H), 1.63–1.42 (m, 4H), 1.30–1.19 (m, 2H), 0.89 (s, 9H). M.S.(electrospray): 241.0 (M−H)− 243.0 (M+H)+. Reverse Phase HPLC Homogeneity (0.06% TFA; CH$_3$CN:H$_2$O): 99%.

Synthesis of Tripeptide 6

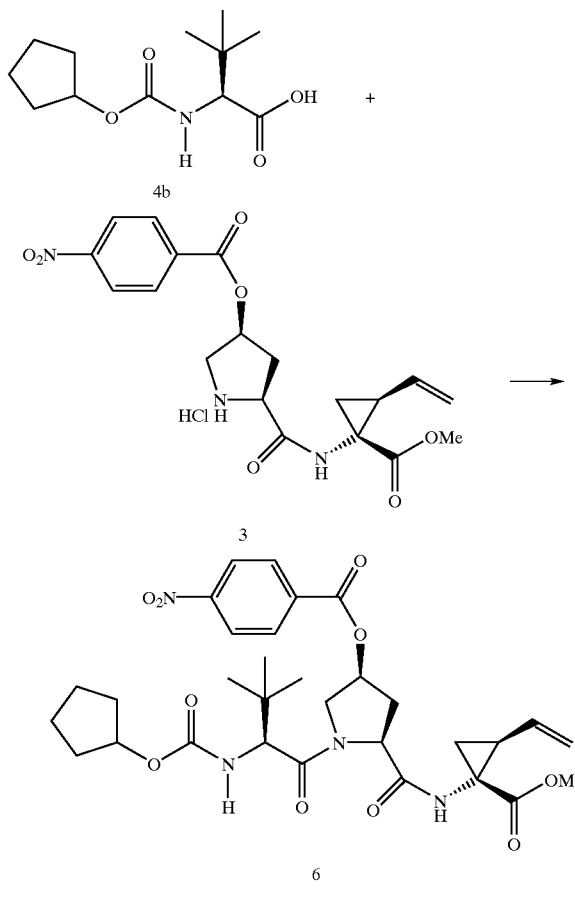

Carbamate 4b (6.15 g, 22.5 mmol) and TBTU (7.72 g, 24.7 mmol) were suspended in DCM and the suspension was stirred rapidly. DIPEA (3.92 mL, 22.5 mmol) was added at R.T. and after 10 min, the reaction was nearly homogeneous. A solution of dipeptide 3 (10.39 g, 23.6 mmol) in anhydrous DCM (1001 mL) containing DIPEA (4.11 mL, 23.62 mmol) was then poured into the reaction. The resulting yellow solution was allowed to stir for 14 h. The solvent was then evaporated yielding a yellow syrup which was extracted with EtOAc (300+150 mL) and washed with 0.05N HCl (2×200 mL), saturated $Na_2CO_3$ (300 mL) and brine (150 mL). The combined extracts were dried over $MgSO_4$ and evaporated to yield the tripeptide 6 as a pale yellow foam (15.68 g, quantitiative).

Synthesis of Tripeptide 7:

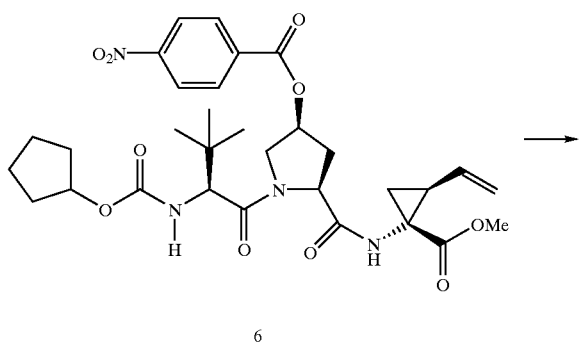

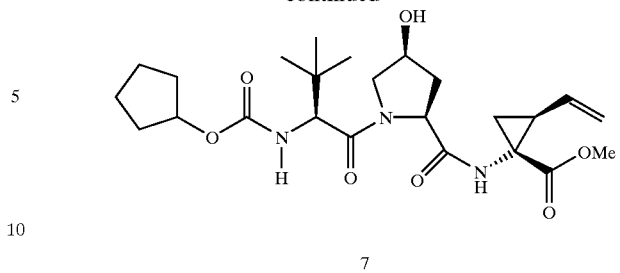

The tripeptide 6 (15.68 g) was dissolved in THF (200 mL) and water (30 mL) was added. The resulting solution was cooled to 0° C. and a solution of lithium hydroxide monohydrate (1.18 g, 28.12 mmol) was added over 3 min with vigorous stirring. After 3 h at 0° C., the excess base was neutralized with 1N HCl (final pH ca. 6) and the THF evaporated, resulting in an aqueous suspension (yellow gum). The mixture was extracted with EtOAc (2×200 mL) and washed with saturated $NaHCO_3$ (2×300 mL). The combined extracts were dried over $MgSO_4$ and evaporated to yield a pale yellow foam. Flash chromatography of the foam over silica gel using EtOAc as eluent afforded 7 as a white amorphous solid (9.77 g, 91%).

Preparation of Thioureas 8
Synthesis of Thiourea 8a:

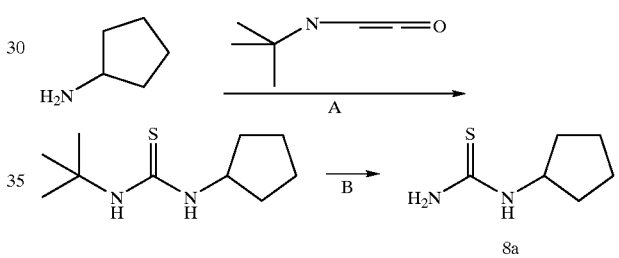

To a solution of tert-butyl isothiocyanate (5.0 mL; 39.4 mmoL) in DCM (200 mL) was added cyclopentylamine (4.67 mL; 47.3 mmoL) followed by DIEA and the reaction mixture was stirred at R.T. for 2 h. The mixture was diluted with EtOAc, washed with a 10% aqueous solution of citric acid (2×), saturated $NaHCO_3$ (2×), $H_2O$ (2×) and brine (1×). The organic layer was dried over anhydrous $MgSO_4$, filtered and evaporated to yield N-tert-butyl-N'-cyclopentyl thiourea as a white solid (3.70 g; 47% yield). The N-tert-butyl-N'-cyclopentyl thiourea (3.70 g) was dissolved in concentrated HCl (46 mL). The dark yellow solution was heated at a gentle reflux. After 40 min the reaction mixture was allowed to cool to R.T. and thereafter cooled in ice and rendered basic to pH 9.5 with solid and a saturated aqueous solution of $NaHCO_3$. The product was extracted into EtOAc (3×). The combined EtOAc extracts were washed with $H_2O$ (2×) and brine (1×). The organic layer was dried ($MgSO_4$), filtered and concentrated to yield a beige solid (2.46 g crude). Trituration of the crude material in hexane/EtOAc 95/5 provided, after filtration, the N-cyclopentythiourea 8a as a white solid (2.38; 90% yield).

$^1$H NMR (400 MHz, DMSO-$d_6$): δ 7.58 (bs, 1H), 7.19 (bs, 1H), 6.76 (bs, 1H), 4.34 (bs, 1H), 1.92–1.79 (m, 2H), 1.66–1.55 (m, 2H), 1.55–1.30 (m,4H). MS; es$^+$ 144.9 (M+H)$^+$, es$^-$: 142.8 (M–H)$^-$.

Preparation of Thiourea 8b
Using the procedure describe above and using commercially available cyclobutylamine instead of cyclopentylamine yielded thiourea 8b:

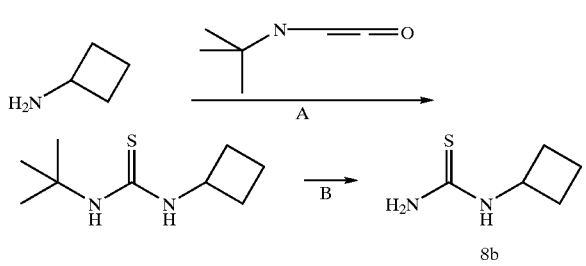

Preparation of Thiourea 8c

Using the procedure describe above and using commercially available cyclohexylamine instead of cyclopentylamine yielded thiourea 8c.

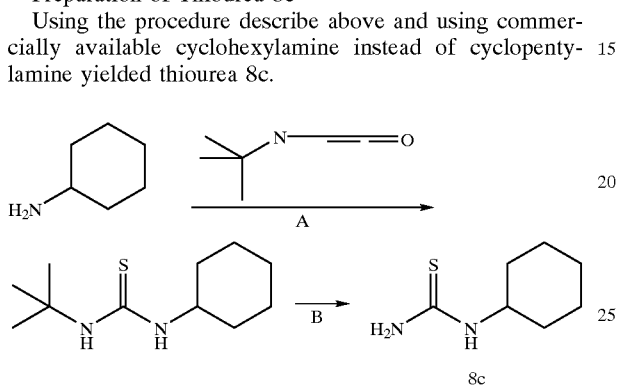

Preparation of Thiourea 8d

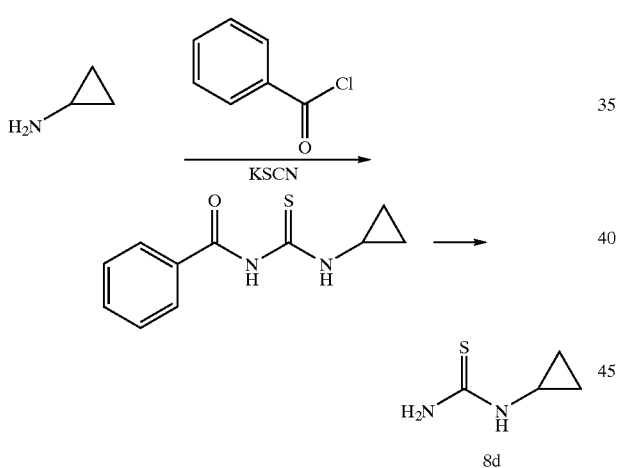

To a solution of the KSCN (4.60 g; 47.33 mmoL) in acetone (35 mL), at 0° C., was added dropwise benzoylchloride (5.0 mL; 43.03 mmoL). The milky solution was stirred in an ice bath for 1.5 h, then, cyclopropylamine (3.2 mL; 46.0 mmoL) was added dropwise. The reaction mixture was stirred for 1.5 h at 0° C., then, more cyclopropylamine (0.50 mL, 7.22 mmoL) was added and the reaction mixture stirred at R.T. for an additional 30 min. The reaction mixture was poured into ice/$H_2O$ (300 mL), stirred for 5 min. and the light yellow solid was filtered, washed several times with $H_2O$ and dried to provide N-benzyloxy-N'-cyclopropyl thiourea (6.62 g). This thiourea was suspended in a solution of 2N NaOH (50 mL) and heated at reflux for 15 min. The solution was cooled to R.T., saturated with solid NaCl and extracted with EtOAc (3×). The combined EtOAc extracts were washed with $H_2O$ (2×) and brine (1×), dried ($MgSO_4$), filtered and evaporated to give the crude product as an off-white solid. The solid was triturated in hexane/EtOAc 5/5 to provide the N-cyclopropyl thiourea 8d as a white crystalline solid (2.5 g; 50% yield).

$^1$H NMR (400 MHz, DMSO-$d_6$): δ 7.92 (bs, 1H), 7.61 (bs, 1H), 7.13 (bs, 1H), 2.39 (bs, 1H), 0.67–0.63 (m, 2H), 0.51–0.44 (m, 2H).

MS; es$^+$ 116.9 (M+H)$^+$, es$^-$: 114.8 (M–H)$^-$.

Example 1

Preparation of Compound 100

Step 1: Synthesis of Tripeptide 10:

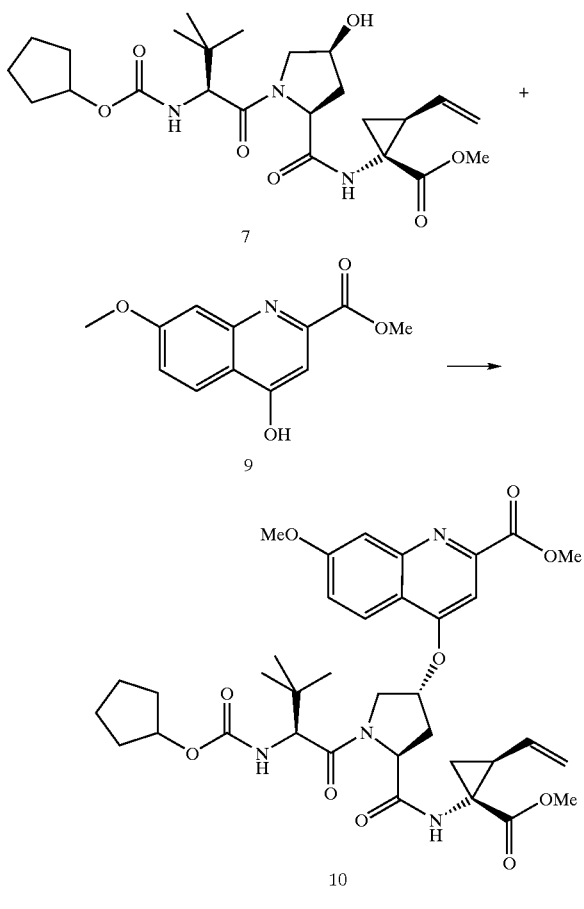

To tripeptide 1 (1.0 g; 2.09 mmol) dissolved in THF (35 mL), hydroxyquinoline 9 (729 mg; 3.13 mmol) and triphenylphosphine (1.1 g; 4.2 mmol) were added. The yellow suspension was cooled in an ice bath and DIAD (821 μL, 4.2 mmol) was added dropwise. The solution was stirred at ice bath temperature for 30 min, and at R.T. for 16 h. The solution was evaporated to dryness and the residue was dissolved in EtOAc, washed with a saturated sodium bicarbonate solution (2×), water (2×) and brine (1×), dried (MgSO4), filtered and evaporated to obtain a yellow oil which precipitated on standing. The crude solid was suspended in DCM and the insoluble material was filtered off. The solution was concentrated and the residue purified by flash chromatography in Hexane:EtOAc; 5:5 to remove all less polar impurities and in $CHCl_3$:EtOAc; 80:20 till all the $Ph_3P$=O has eluted. The desired compound was eluted with $CHCl_3$:EtOAc; 65:35 as a white solid (1 g; 70% yield). M.S.(electrospray): 693.3 (M−H)− 695.4 (M+H)+ 717.4 (M+Na)+. Reverse Phase HPLC Homogeneity (0.06% TFA; $CH_3CN$:$H_2O$): 99%.

Step 2: Selective Monohydrolysis of Ester 10:

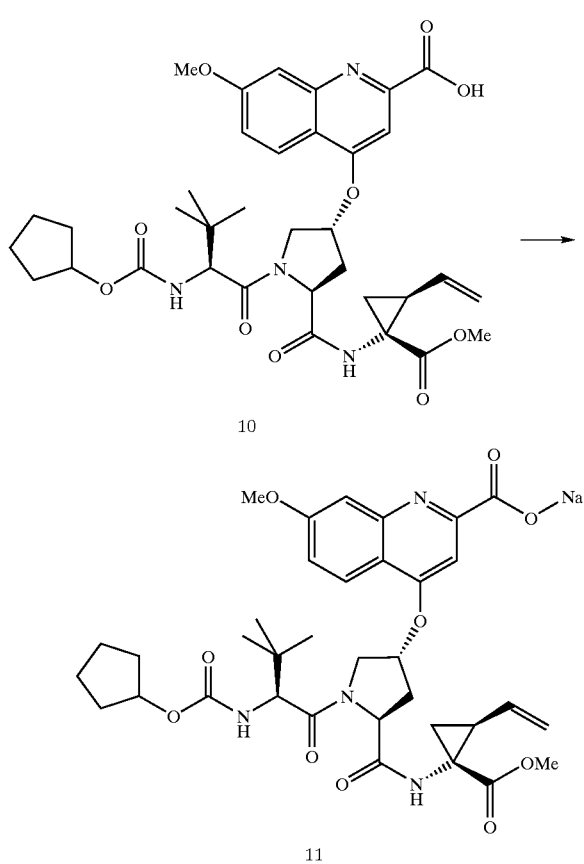

Tripeptide 10 (1 g; 1.44 mmol) was dissolved in THF (10 mL) and MeOH (5 mL), water (5 mL) and a 1N NaOH aqueous solution (1.5 mL) were added and the solution stirred at R.T. for 2 h. The mixture was evaporated to dryness and then coevaporating with MeOH:toluene (1:1; 4×), toluene (2×) and diethyl ether (2×) to obtain the product (water-free) as a white flaky solid (1.04 g; 100% yield) M.S.(electrospray): 679.3 (M−H)− 681.3 (M+H)+ 703.3 (M+Na)+. Reverse Phase HPLC Homogeneity (0.06% TFA; CH$_3$CN:H$_2$O): 95%.

Step 3: Synthesis of Diazoketone 12:

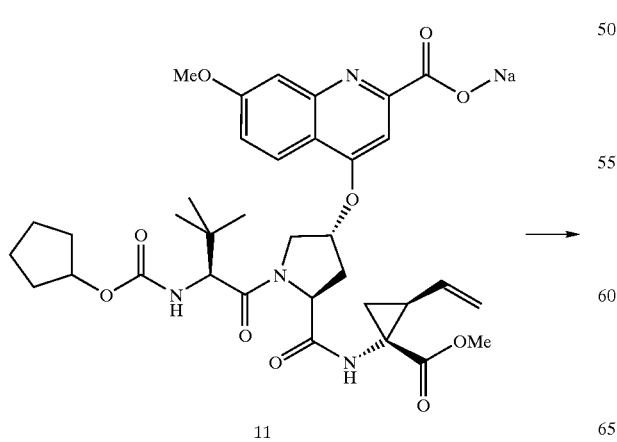

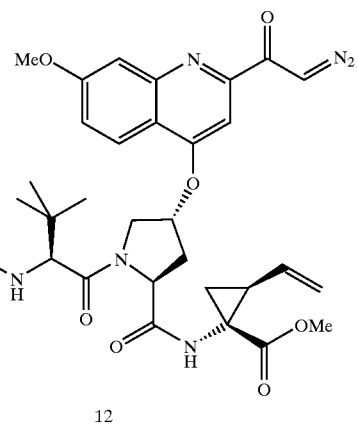

Sodium salt 11 (assume 1.44 mmol) was dissolved in THF (16 mL), triethylamine (301 μL; 2.16 mmol) was added and the solution cooled to 0° C. Isobutylchloroformate (280 μL; 2.16 mmol) was added dropwise and the white suspension was stirred at 0° C. for 75 min, followed by the addition of a solution of diazomethane (0.67M in diethyl ether; 13 mL; 8.64 mmol). The reaction mixture is stirred 1 h at 0° C., 45 min at R.T. and evaporated to provide a thick suspension. This suspension was dissolved in EtOAc and water. The organic solution was washed with saturated NaHCO$_3$ (2×), water (2×) and brine (1×), dried (MgSO4), filtered and evaporated to give the diazoketone product as an ivory solid (crude material used for next step; assume 1.44 mmol).

M.S.(electrospray): 703.3 (M−H)− 705.3 (M+H)+. Reverse Phase HPLC Homogeneity (0.06% TFA; CH$_3$CN:H$_2$O): 91%.

Step 4: Synthesis of Bromoketone 13:

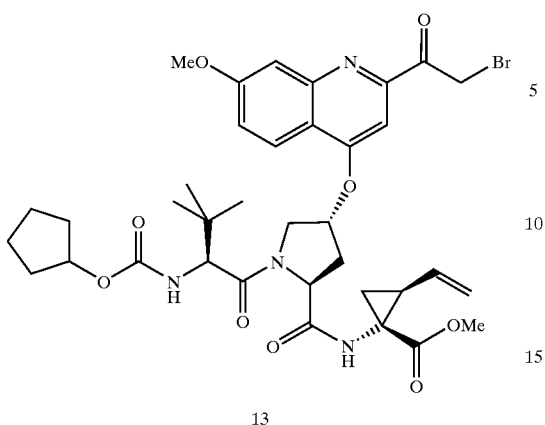

13

At 0° C., to a solution of diazoketone 12 (1.44 mmol) in THF (24 mL) was added dropwise an HBr solution (1.0 mL) and the mixture was stirred for 1 h. The solution was diluted with EtOAc, washed with a saturated NaHCO$_3$ solution(2×), water (2×) and brine (1×), dry (MgSO4), filtered and evaporated to give the desired bromoketone as an ivory-beige solid (1.1 g; assume 1.44 mmol).

M.S.(electrospray): 757.3 (M) 759.3 (M+2).

Step 5: Synthesis Thiazolyl Tripeptide 14:

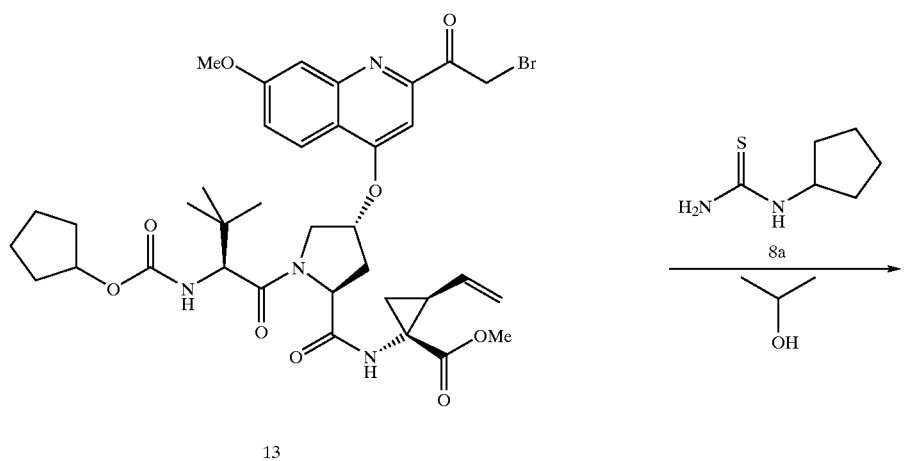

13

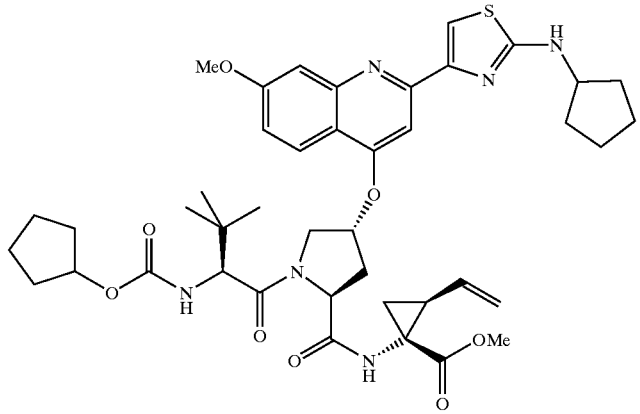

14

α-Bromoketone 13 (0.40 mmol) and N-cyclopentylthiourea (68.5 mg; 0.48 mmol) were dissolved in isopropanol (15 mL) and the yellow solution was heated at 70° C. for 75 min. The solution was allowed to cool to R.T., and evaporated to dryness. The residue was dissolved in EtOAc. The solution was washed with saturated NaHCO$_3$ (2x), water (2x) and brine (1x), dried (MgSO4), filtered and concentrated to give the product as an orange-brown foam. Flash column chromatography in hexane:EtOAc 7:3 removed less polar impurities and 6:4 retrieved the desired compound as a light yellow foam (218 mg; 69%).

M.S.(electrospray): 801.4 (M–H)– 803.4 (M+H)+ 825 (M+Na)+. Reverse Phase HPLC Homogeneity (0.06% TFA; CH$_3$CN:H$_2$O): 99%.

Step 6: Hydrolysis of Ester 14:

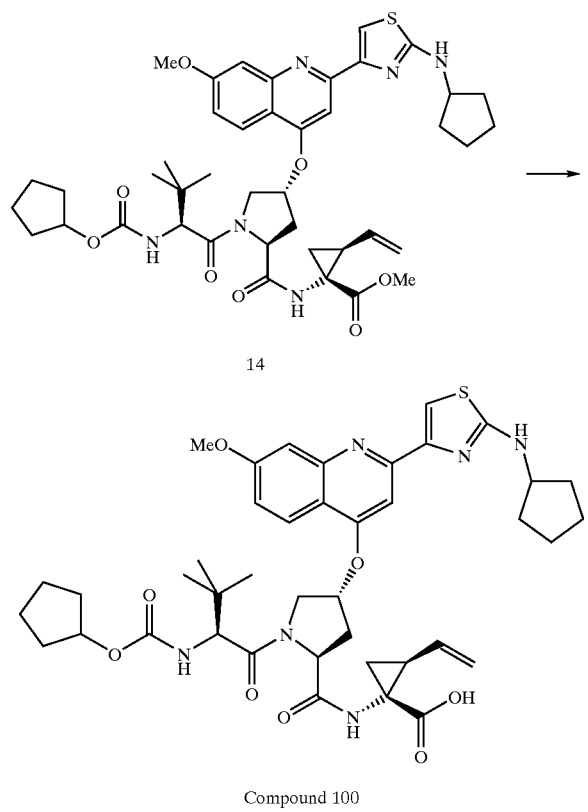

Compound 100

A solution of methyl ester 14 (145 mg; 0.181 mmol) in THF (3 mL), MeOH (1.5 mL) and an aqueous solution of LiOH (75.8 mg; 1.81 mmol) in water (1.5 mL) was stirred for 18 h. The organic solution was concentrated to provide an off-white suspension which was diluted with EtOAc and brine to obtain a total solution. The pH was adjusted to 6 by the addition of 1N HCl and the organic layer was extracted further with EtOAc (2x). The combined organic extracts were washed with water (2x), brine (1x), dried (MgSO4), filtered and evaporated to give the desired compound as a yellow solid (138.2 mg; 97% yield).

Conversion to Na Salt

Compound 100 (138.2 mg; 0.175 mmol) was dissolved in MeOH (30 mL) and 1 equivalent 0.01N NaOH (17.5 mL) was added. The clear yellow solution was concentrated to remove MeOH and diluted with water, frozen and lyophilized to obtain the product (Na salt) as a yellow amorphous solid (139 mg; theoretical yield: 142 mg; MW Na salt: 810.95).

M.S.(electrospray): 787.2 (M–H)– 789.3 (M+H)+ 811.3 (M+Na)+. Reverse Phase HPLC Homogeneity (0.06% TFA; CH$_3$CN:H$_2$O): 98%. $^1$H NMR (400 MHz, DMSO-d$_6$): ca, 5:1 mixture of rotamers; δ 8.14 (bs, 1H), 8.02 (d, J=9.2 Hz, 1H), 7.89 (d, J=6.7 Hz, 1H), 7.49–7.36 (m, 2H), 7.27 (bs, 1H), 7.06–6.96 (m, 2H), 6.10–5.90 (m, 1H), 5.33 (s, 1H), 5.01 (d, J=16.8 Hz, 1H), 4.84 (d, J=10.6 Hz, 1H), 4.79–4.65 (m, 1H), 4.47–4.40 (m, 1H), 4.30 (d, J=11.5 Hz, 1H),), 4.15 (d, J=8.8 Hz, 1H), 4.00–3.85 (m, 2H), 3.90 (s, 3H), 2.37–2.26 (m, 1H), 2.15–1.91 (m, 2H), 1.80–1.23 (m, 18H), 0.96 & 0.86 (2xs, 9H).

Example 2

Preparation of Compound 101

Using the same procedure described in example 1 and using N-cyclobutyl thiourea 8b instead of using N-cyclopentyl thiourea 8a in step 5 and resulted in compound 101 as the TFA salt:

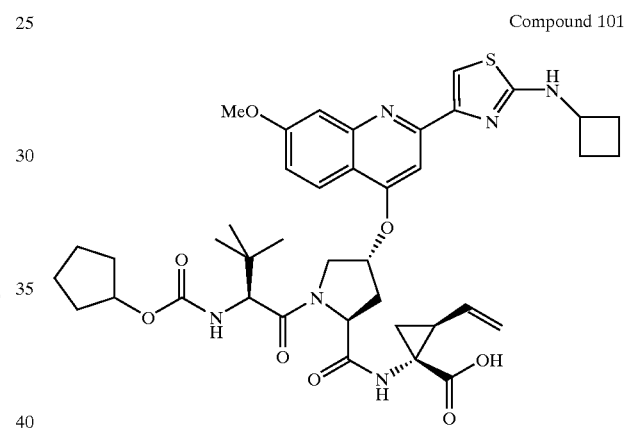

Compound 101

$^1$H NMR (400 MHz, DMSO-d$_6$): ca, 90:10 mixture of rotamers, major isomer description; δ 8.59 (s, 1H), 8.45–8.39 (m, 1H), 8.25 (bs, 1H), 8.20 (d, J=9.2 Hz, 1H), 7.84 (bs, 1H), 7.74 (s, 1H), 7.32–7.26 (m, 1H), 7.01 (d, J=8.3 Hz, 1H), 5.78–5.66 (m, 2H), 5.20 (dd, J=17.0, 1.6 Hz, 1H), 5.09–5.04 (m, 1H), 4.53–4.36 (m, 4H), 4.05–3.92 (m, 2H), 3.97 (s, 3H), 2.63–2.55 (m, 1H), 2.44–2.29 (m, 3H), 2.07–1.95 (m, 3H), 1.79–1.23 (m, 12H), 0.96 (s, 9H).

M.S.(electrospray): 773.4 (M–H)– 775.4 (M+H)+. Reverse Phase HPLC Homogeneity (0.06% TFA; CH$_3$CN:H$_2$O): 98%.

Example 3

Preparation of Compound 102

Using the same procedure described in example 1 and using N-cyclohexyl thiourea 8c instead of using N-cyclopentyl thiourea 8a in step 5 and resulted in compound 102 as the TFA salt:

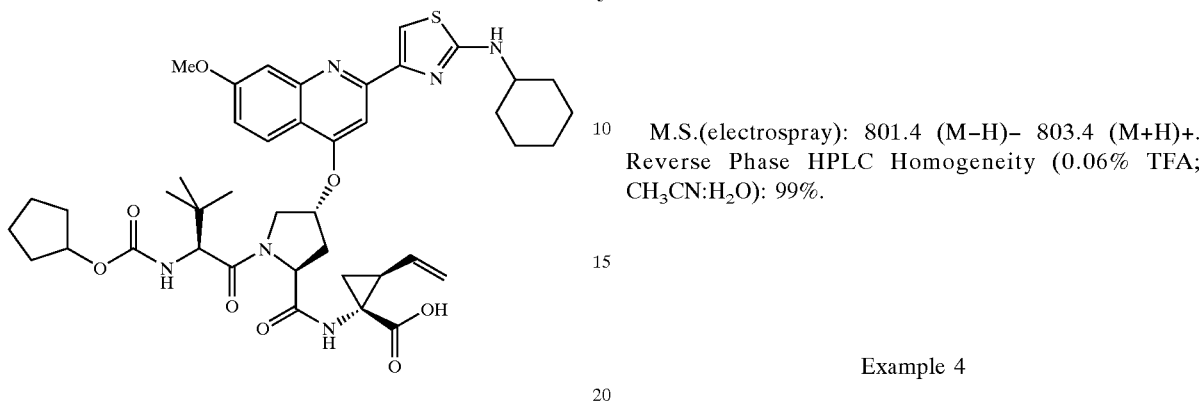
Compound 102
$^1$H NMR (400 MHz, DMSO-d$_6$): ca, 90:10 mixture of rotamers, major isomer description; δ 8.61 (s, 1H), 8.26–8.17 (m, 2H), 8.13–8.04 (m, 1H), 7.81 (bs, 1H), 7.73 (bs, 1H), 7.32–7.24 (m, 1H), 7.07 (d, J=8.2 Hz, 1H), 5.78–5.65 (m, 2H), 5.23–5.15 (m, 1H), 5.09–5.03 (m, 1H), 4.51–4.43 (m, 3H), 4.05–3.77 (m, 3H), 3.97 (s, 3H), 2.64–2.55 (m, 1H), 2.38–2.27 (m, 1H), 2.05–1.95 (m, 3H), 1.79–1.71 (m, 2H), 1.66–1.19 (m, 16H), 0.96 (s, 9H).
M.S.(electrospray): 801.4 (M−H)− 803.4 (M+H)+. Reverse Phase HPLC Homogeneity (0.06% TFA; CH$_3$CN:H$_2$O): 99%.
Example 4
Preparation of Compound 103
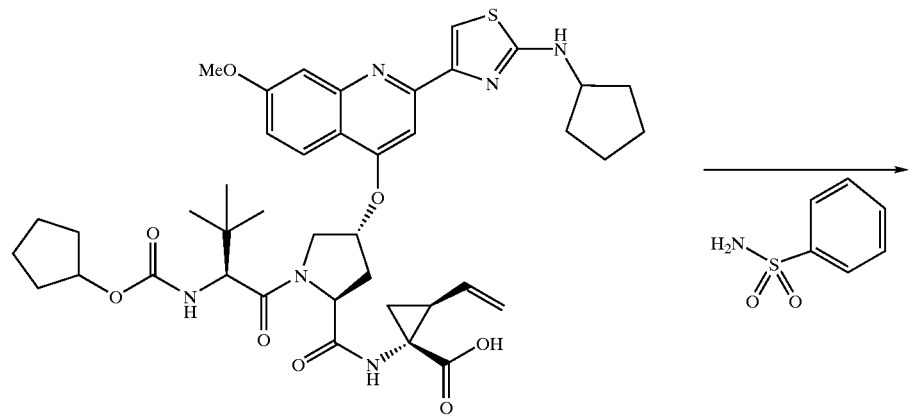
Compound 100
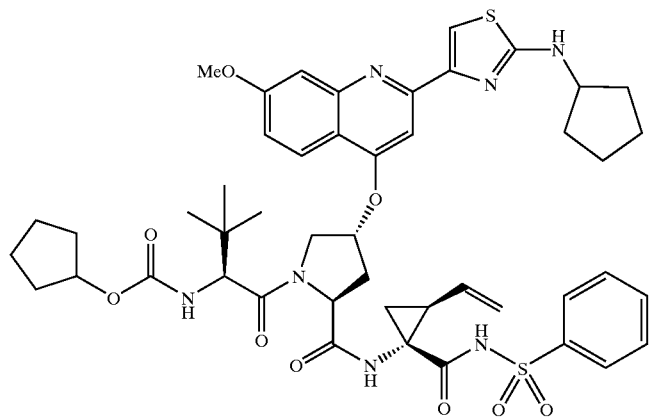
Compound 103

Compound 100 (30 mg, 0.038 mmol) was combined with HATU (17 mg, 0.045 mmol) and dissolved in anhydrous DMF (4 mL). The solution was stirred at R.T. before DIPEA (26 µL, 0.15 mmol) was added dropwise over ca. 1 min. The mixture was stirred for 60 min. at R.T. and analyzed by analytical HPLC for the formation of the activated ester. Following this, a solution of benzenesulfonamide (23 mg, 0.15 mmol), DMAP (17 mg, 0.14 mmol) and DBU (22 µL, 0.15 mmol) was added in DMF (1 mL). The reaction mixture was stirred 24 h at R.T. before being poured into EtOAc (50 mL) and washed with sat. NaHCO$_3$, and sat. brine solutions. The organic phase was dried over MgSO$_4$, filtered and concentrated. The residue was reconstituted in DMSO and purified by preparative HPLC. Lyophilization gave the final product (17 mg, 48%) as a pale yellow amorphous solid.

$^1$H-NMR (400 MHz, DMSO-d6), δ 10.89 (s, 1H), 8.84 (s, 1H), 8.20 (d, J=8.8 Hz, 1H), 8.18–8.08 (m, 2H), 7.89 (d, J=7.6 Hz, 2H), 7.70 (dd, J=7.6, 7.6 Hz, 2H), 7.58 (dd, J=7.7, 7.7 Hz, 2H), 7.28 (bs, 1H), 7.11 (d, J=6.6 Hz, 1H), 5.75 (bs, 1H), 5.37–5.25 (m, 1H), 5.12 (d, J=17 Hz, 1H), 4.92 (d, J=12 Hz, 1H), 4.58–4.42 (m, 3H), 4.24 (bs, 1H), 4.05 (d, J=7.8 Hz, 1H), 3.97 (s, 3H), 3.93 (d, J=7.8 Hz, 1H), 2.69–2.61 (m, 1H), 2.35–2.21 (m, 1H), 2.13–1.98 (m, 3H), 1.78–1.68 (m, 4H), 1.68–1.51 (m, 8H), 1.50–1.41 (m, 4H), 1.29–1.22 (m, 1H), 0.99 (s, 9H).

MS (electrospray): 928.5 (M +H)+, and 926.5 (M–H)–.

RP-HPLC: Rt=7.3 minutes (homogeneity=99%).

Using the synthetic sequence shown in Scheme 2 the following compounds were prepared:

Example 5

Step 1: Synthesis of Dipeptide 16:

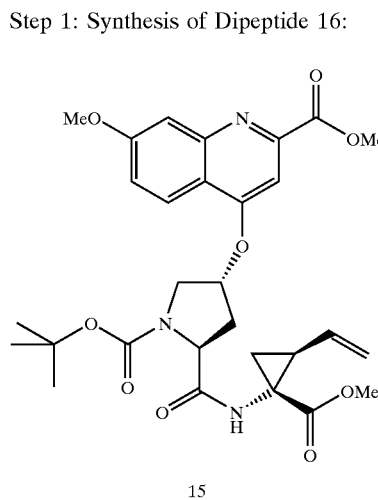

15

→

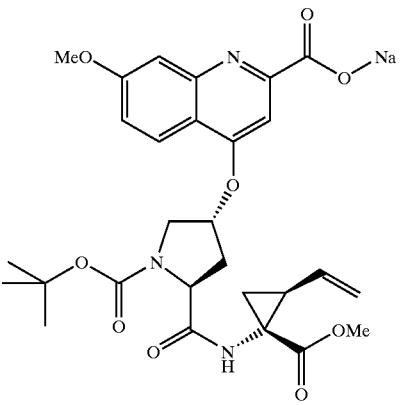

16

Dipeptide 15 (4.0 g; 7.02 mmol) was dissolved in THF (20 mL) and MeOH (10 mL), water (10 mL) and a 1N NaOH aqueous solution (1.05 equivalents; 7.4 mL) was added. The solution stirred at R.T. for 2.75 h. The mixture was evaporated to dryness. The residue was diluted with water, frozen and lyophilized to provide sodium salt 16 as a white amorphous solid (4.28 g).

M.S.(electrospray): 554.2 (M–H)– 556.3 (M+H)+ 578.2 (M+Na)+. Reverse Phase HPLC Homogeneity (0.06% TFA; CH$_3$CN:H$_2$O): 96%.

Step 2: Synthesis of Dipeptide Diazoketone 17:

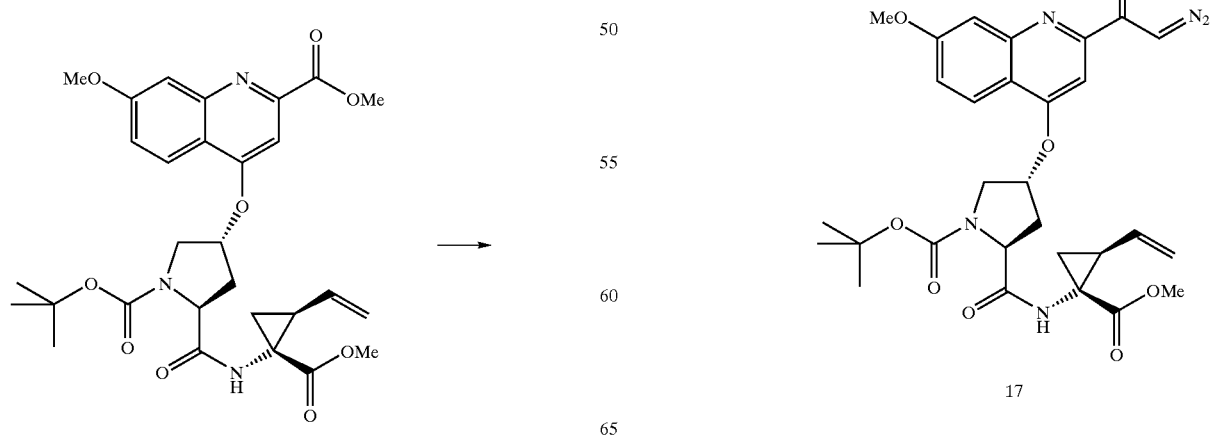

Sodium salt 16 (assume 7.02 mmol) was dissolved in THF (78 mL); triethylamine (1.37 mL; 9.83 mmol) was added and the solution cooled to 0° C. Isobutylchloroformate (1.28 mL; 9.83 mmol) was added dropwise and the white suspension was stirred at 0° C. for 2 h, followed by the addition of a solution of diazomethane (0.67M in diethyl ether; 63 mL; 42.13 mmol). The reaction mixture was stirred 1 h at 0° C., 1.25 h at R.T. and evaporated to provide a thick suspension. This suspension was dissolved in EtOAc and water. The organic solution was washed with saturated NaHCO$_3$ (2×), water (2×) and brine (1×), dried (MgSO4), filtered and evaporated to give the diazoketone 17 as an beige solid (crude material used for next step; assume 7.02 mmol).

M.S.(electrospray): 578.2 (M−H)− 580.3 (M+H)+. Reverse Phase HPLC Homogeneity (0.06% TFA; CH$_3$CN:H$_2$O): 90%.

Step 3: Synthesis of Dipeptide Bromoketone 18:

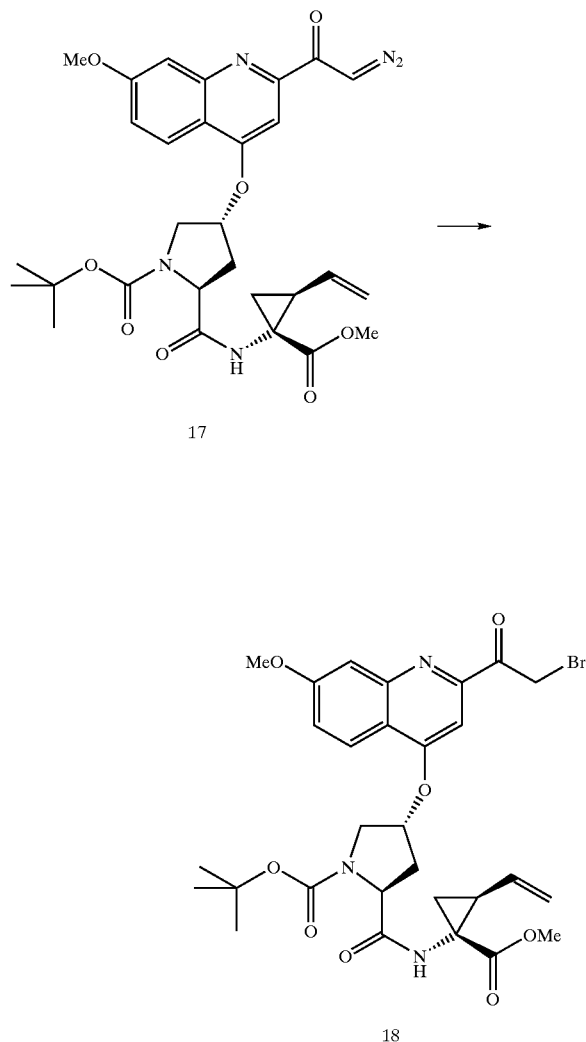

At 0° C., to a solution of diazoketone (assume 1.44 mmol) in THF (116 mL) was added dropwise a 48% aqueous HBr solution (5.1 mL) and the mixture was stirred for 2 h. The solution was diluted with EtOAc, washed with a saturated NaHCO$_3$ solution(2×), water (2×) and brine (1×), dry (MgSO4), filtered and evaporated to give the desired bromoketone as a beige solid (4.25 g; 6.72 mmol).

M.S.(electrospray): 632 (M) 634.2 (M+2).

Step 4: Synthesis of Dipeptide 19:

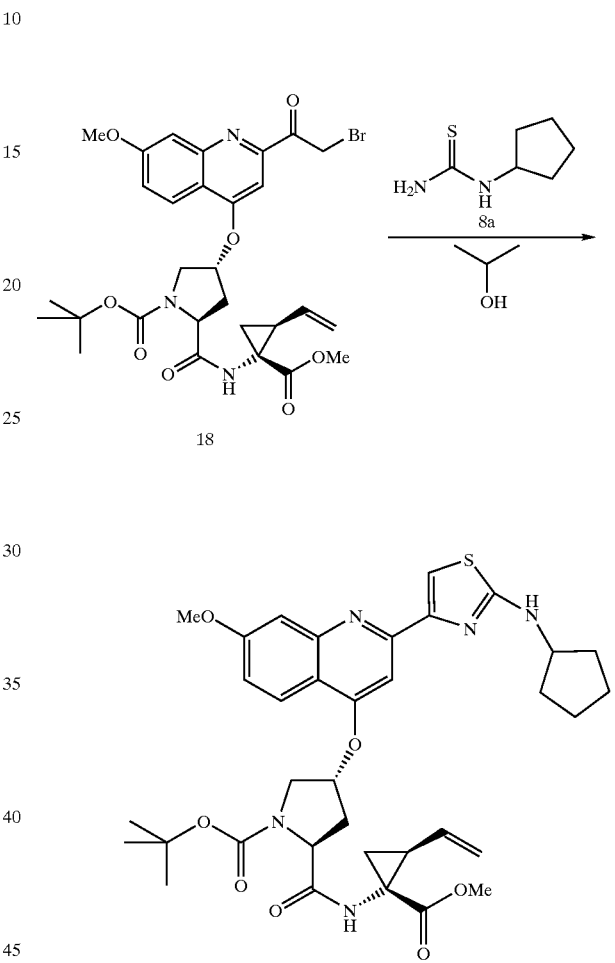

α-Bromoketone 18 (512 mg; 0.81 mmol) and N-cyclopentylthiourea (128.4 mg; 0.89 mmol) were dissolved in isopropanol (20 mL). The resulting yellow solution was heated at 70° C. for 1.5 h. The solution was allowed to cool to R.T., and evaporated to dryness. The residue was diluted with EtOAc. The EtOAc solution was washed with saturated NaHCO$_3$ (2×), water (2×) and brine (1×), dried (MgSO4), filtered and concentrated to give the product as an orange-brown foam. Flash column chromatography in hexane:EtOAc 7:3 removed less polar impurities and 6:4 retrieved the desired compound as a light yellow solid (411.5 mg; 75%).

M.S.(electrospray): 676.3 (M−H)− 678.3 (M+H)+ Reverse Phase HPLC Homogeneity (0.06% TFA; CH$_3$CN:H$_2$O): 99%.

Step 5: Synthesis of Tripeptide 20:

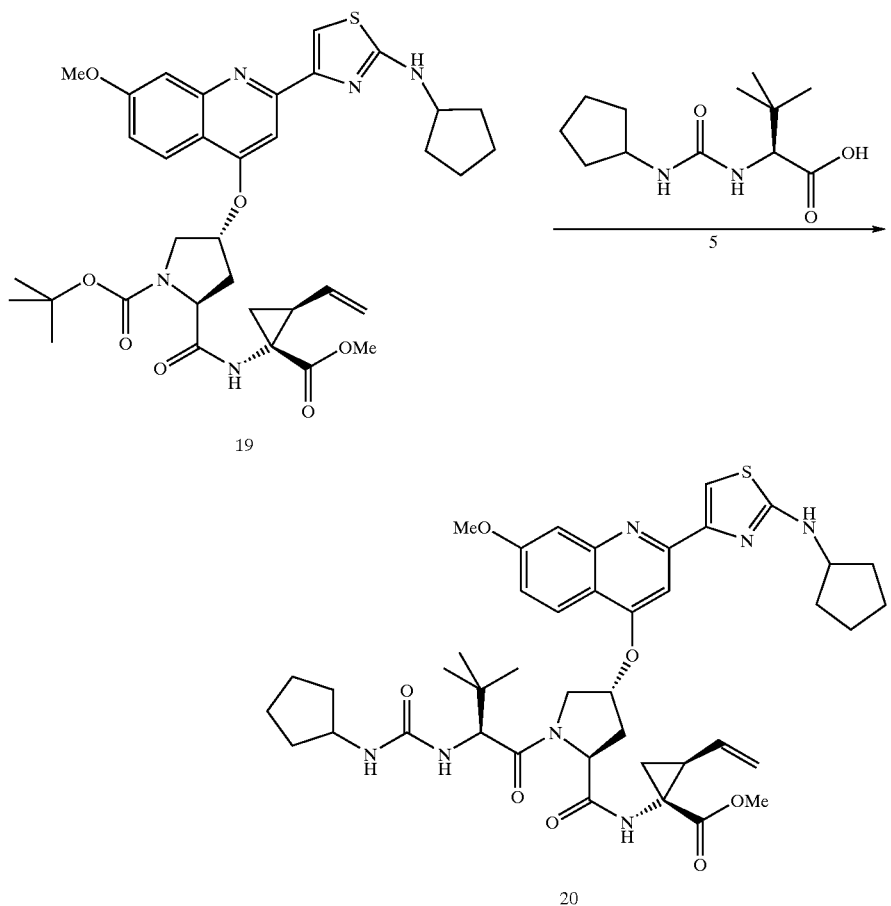

The Boc-dipeptide (32.6 g; 0.048 mmol) was dissolved in 4N HCl/dioxane (3 mL) and stirred at R.T. After 2 h, the reaction mixture was worked-up by evaporating to dryness. The HCl salt thus obtained as an off-white solid. The HCl salt was subjected to high vacuum for 30 min. To a solution of the HCl salt in DCM (2 mL) and DIEA (33 μL; 0.192 mmol), was added urea 5 (13.96 mg; 0.058 mmol), followed by HATU coupling agent (21.90 mg; 0.058 mmol). The reaction mixture was stirred at R.T. for 3 h. The reaction mixture was diluted with EtOAc, washed with saturated NaHCO$_3$ (2×), water (2×) and brine (1×), dried (MgSO4), filtered and evaporated to give the crude product as a thick yellow oil (assume 0.048 mmol).

M.S. (electrospray): 800.4 (M−H)− 802.4 (M+H)+. Reverse Phase HPLC Homogeneity (0.06% TFA; CH$_3$CN:H$_2$O): 95%.

Step 6: Hydrolysis of Tripeptide Methyl Ester 20:

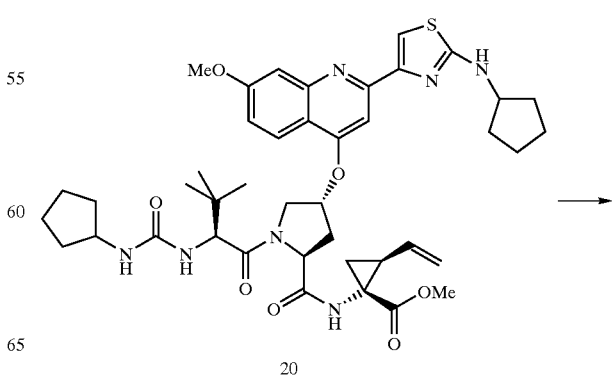

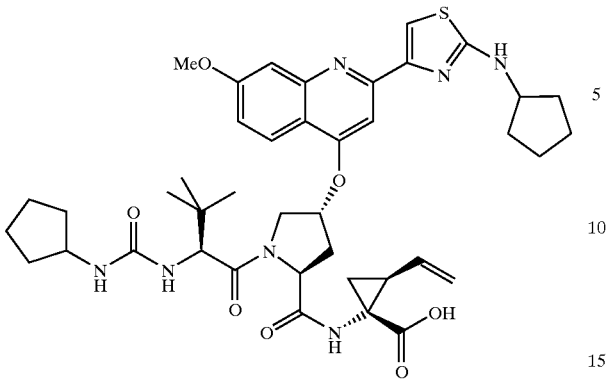

Compound 104 (shown at top left)

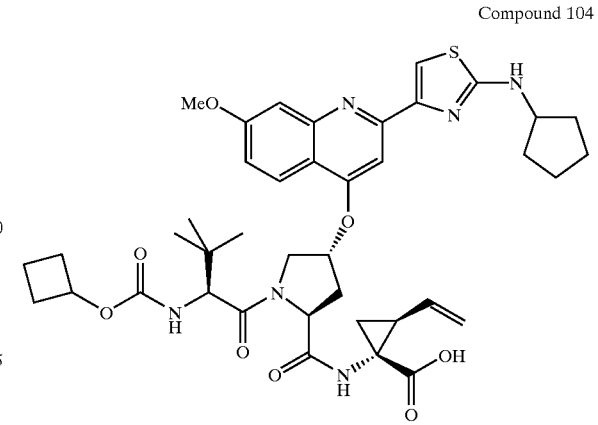

Compound 104

A solution of methyl ester 20 (77.80 mg; 0.097 mmol) in THF (2 mL), and MeOH (1 mL), and an aqueous solution of LiOH (40.7 mg; 0.97 mmol) in water (1 mL), was stirred for 16 h. The organic solution was concentrated to provide an off-white suspension. The crude material was purified by preparatory HPLC (YMC Combiscreen ODS-AQ, 50×20 mm ID S-5micron, 120A; λ=220 nm) using a linear gradient and 0.06% TFA $CH_3CN/H_2O$. The pure fractions were combined, concentrated and converted to the sodium salt.

Conversion to Na Salt

The concentrated fractions were diluted with EtOAc and a few mls of brine, (basified to pH~13 with 5N NaOH, then, neutralized to pH 5.5 –6.0 with 1N HCl). The product was extracted with EtOAc (3×), washed with water (2×) and brine (1×), dried ($MgSO_4$), filtered and evaporated to dryness to provide the neutral product as a yellow solid (52.7 mg; 70%). The neutral product (49.4 mg; 0.0627 mmol) was dissolved in MeOH (10 mL) and 1 equivalent 0.01N NaOH (6.27 mL) was added.

The clear yellow solution was concentrated to remove MeOH and diluted with water, frozen and lyophililzed to give the product (Na salt) as a yellow amorphous solid (50.8 mg; theoretical yield: 50.8 mg; MW Na salt: 809.75)

$^1$H NMR (400 MHz, DMSO-$d_6$): ca, 8:1 mixture of rotamers;δ 8.20 (bs, 1H), 7.96 (d, J=8.8 Hz, 1H), 7.86 (d, J=5.7 Hz, 1H), 7.51–7.47 (m, 2H), 7.26 (s, 1H), 6.97 (d, J=8.6 Hz, 1H), 6.19–6.02 (m, 1H), 5.33 (bs, 1H), 4.99 (d, J=16.8 Hz, 1H), 4.77 (d, J=10.0 Hz, 1H), 4.52–4.41 (m, 2H), 4.34 (d, J=11.0 Hz, 1H),), 4.04–3.96 (m, 2H), 3.89 (s, 3H), 3.79–3.68 (m, 1H), 3.68–3.15 (under water peak, 2H), 2.45–2.36 (m, 1H), 2.05–1.92 (m, 2H), 1.82–1.35 (m, 16H), 1.35–1.12 (m, 2H), 0.91 & 0.84 (2×s, 9H).

M.S.(electrospray): 786.4 (M–H)– 788.3 (M+H)+ 810 (M+Na)+. Reverse Phase HPLC Homogeneity (0.06% TFA; $CH_3CN:H_2O$): 99%.

Example 6

Compound 104

Using the same procedure as described in example 6 and using the cyclobutyl carbamate of tert-butyl glycine in step 5 instead of urea 5 and purifying the crude carboxylic acid after step 6 by preparative HPLC afforded the title compound as a TFA salt:

$^1$H NMR (400 MHz, DMSO-$d_6$): ca, 7:1 mixture of rotamers; δ 8.09 (bs, 1H), 8.02 (d, J=9.0 Hz, 1H), 7.88 (d, J=6.5 Hz, 1H), 7.45 (s, 1H), 7.40 (s, 1H), 7.28 (d, J=2.3 Hz, 1H), 7.16–7.08 (m, 1H), 7.07–7.00 (m, 1H), 6.10–5.95 (m, 1H), 5.32 (bs, 1H), 5.00 (d, J=17.2 Hz, 1H), 4.82 (d, J=11.4 Hz, 1H), 4.64–4.52 (m, 1H), 4.48–4.41 (m, 1H), 4.29 (d, J=11.7 Hz, 1H),), 4.12 (d, J=8.6 Hz, 1H), 3.97–3.85 (m, 2H), 3.91 (s, 3H), 2.36–2.27 (m, 1H), 2.18–2.04 (m, 2H), 2.03–1.81 (m, 6H), 1.77–1.43 (m, 9H), 1.41–1.34 (m, 1H), 0.96 & 0.85 (2×s, 9H).

M.S.(electrospray): 773.3 (M–H)– 775.4 (M+H)+. Reverse Phase HPLC Homogeneity (0.06% TFA; $CH_3CN:H_2O$): 99%.

Example 7

Compound 105

Using the same procedure as described in example 6 and using the cyclohexyl carbamate of tert-butyl glycine in step 5 instead of urea 5 afforded the title compound as the sodium salt:

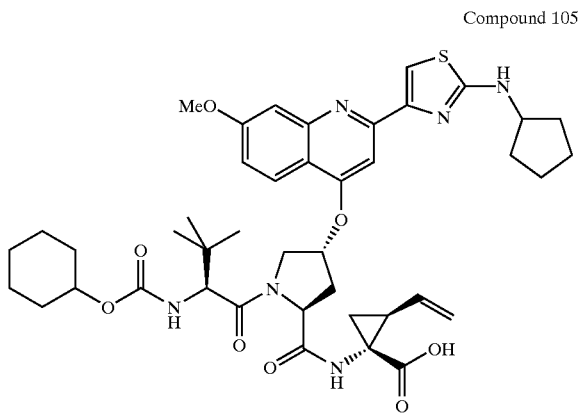

Compound 105

$^1$H NMR (400 MHz, DMSO-$d_6$): ca, 5:1 mixture of rotamers; δ 8.29 (bs, 1H), 8.02 (d, J=9.0 Hz, 1H), 7.89 (d, J=6.5 Hz, 1H), 7.45 (s, 1H), 7.40 (s, 1H), 7.27 (d, J=2.2 Hz, 1H), 7.05 (d, J=8.6 Hz, 1H), 7.00 (dd, J=2.0, 9.0 Hz, 1H), 5.89 (bs, 1H), 5.34 (s, 1H), 5.08 (d, J=17.0 Hz, 1H), 4.91 (d, J=9.4 Hz, 1H), 4.43 (dd, J=8.4, 16.8 Hz, 1H), 4.36–4.24 (m, 1H), 4.14 (d, J=8.6 Hz, 1H),), 4.00–3.86 (m, 3H), 3.89 (s, 3H), 2.35–2.23 (m, 1H), 2.04–1.91 (m, 5H), 1.79–1.41 (m, 10H), 1.39–1.08 (m, 7H), 0.97 & 0.86 (2×s, 9H).

M.S.(electrospray): 801.4 (M−H)− 803.4 (M+H)+. Reverse Phase HPLC Homogeneity (0.06% TFA; CH₃CN:H₂O): 98%.

Example 8

Compound 106

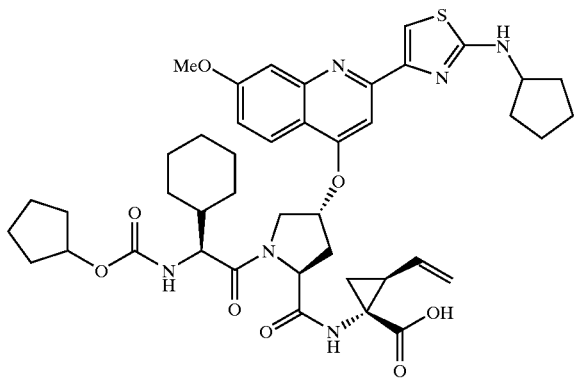

Using the same procedure as described in example 6 and using the cyclopentyl carbamate of cyclohexyl glycine in step 5 instead of urea 5 afforded the title compound as the sodium salt:

$^1$H NMR (400 MHz, DMSO-d$_6$): ca, 1: 4 mixture of rotamers; δ 8.22 & 8.04 (2×s, 1H), 8.00 (d, J=9.2 Hz, 1H), 7.91 (d, J=6.5 Hz, 1H), 7.46 (s, 1H), 7.41 (s, 1H), 7.27 (d, J=2.4 Hz, 1H), 7.20 (d, J=8.4 Hz, 1H), 7.01 (dd, J=2.4, 9.0 Hz, 1H), 6.09–5.98 (m, 1H), 5.34 (s, 1H), 4.98 (dd, J=1.6, 17.4 Hz, 1H), 4.80 (d, J=11.9 Hz, 1H), 4.73–4.67 (m, 1H), 4.43–4.31 (m, 2H), 4.05–3.95 (m, 2H), 3.95–3.84 (m, 1H), 3.90 (s, 3H), 2.38–2.29 (m, 1H), 2.03–1.92 (m, 2H), 1.83–1.21 (m, 24H), 1.21–0.83 (m, 5H).

M.S.(electrospray): 813.4 (M−H)− 815.4 (M+H)+. Reverse Phase HPLC Homogeneity (0.06% TFA; CH₃CN:H₂O): 99%.

Example 9

Compound 107

Using the same procedure as described in example 6 and using the cyclopentyl carbamate of cyclopentyl glycine instead of urea 5 in step 5, afforded the title compound which was converted to its corresponding Na salt (entry #13 in TABLE 1 hereinafter).

Example 10

NS3-NS4A Protease Assay

The enzymatic assay used to evaluate the present compound is described in WO 00/09543 and WO 00/59929.

Example 11

Cell Based HCV RNA Replication Assay

Cell Culture

Huh7 cells that stably maintain a subgenomic HCV replicon were established as previously described (Lohman et al., 1999. Science 285: 110–113) and designated as the S22.3 cell-line. S22.3 cells are maintained in Dulbecco's Modified Earle Medium (DMEM) supplemented with 10% FBS and 1 mg/mL neomycin (Standard Medium). During the assay, DMEM medium supplemented with 10% FBS, containing 0.5% DMSO and lacking neomycin was used (Assay Medium). 16 hours prior to compound addition, S22.3 cells are trypsinized and diluted to 50 000 cells/ml in Standard Medium. 200 μL (10 000 cells) are distributed into each well of a 96-well plate. The plate was then incubated at 37° with 5% CO₂ until the next day.

Reagents and Materials

| Product | Company | Catalog # | Storage |
|---|---|---|---|
| DMEM | Wisent Inc. | 10013CV | 4° C. |
| DMSO | Sigma | D-2650 | RT |
| Dulbecco's PBS | Gibco-BRL | 14190-136 | RT |
| Fetal Bovine Serum | Bio-Whittaker | 14-901F | −20° C./4° C. |
| Neomycin (G418) | Gibco-BRL | 10131-027 | −20° C./4° C. |
| Trypsin-EDTA | Gibco-BRL | 25300-054 | −20° C./4° C. |
| 96-well plates | Costar | 3997 | RT |
| PVDF 0.22 μm Filter Unit | Millipore | SLGV025LS | RT |
| Deep-Well Titer Plate Polypropylene | Beckman | 267007 | RT |

Preparation of Test Compound

10 μL of test compound (in 100% DMSO) was added to 2 ml of Assay Medium for a final DMSO concentration of 0.5% and the solution was sonicated for 15 min and filtered through a 0.22 μM Millipore Filter Unit. 900 μl was transfered into row A of a Polypropylene Deep-Well Titer Plate. Rows B to H, contain 400 μL aliquots of Assay Medium (containing 0.5% DMSO), and are used to prepare serial dilutions (1/2) by transferring 400 μl from row to row (no compound was included in row H).

Application of Test Compound to Cells

Cell culture medium was aspirated from the 96-well plate containing the S22.3 cells. 175 μL of assay medium with the appropriate dilution of test compound was transferred from each well of the compound plate to the corresponding well of the cell culture plate (row H was used as the "No inhibition control"). The cell culture plate was incubated at 37° with 5% CO₂ for 72 h.

Extraction of Total Cellular RNA

Following the 72 h incubation period, the total cellular RNA was extracted from the S22.3 cells of the 96-well plate using the RNeasy 96 kit (Qiagen®, RNeasy Handbook. 1999.). Briefly, assay medium was completely removed from cells and 100 μL of RLT buffer (Qiagen®) containing 143 mM β-mercaptoethanol was added to each well of the 96-well cell-culture plate. The microplate was gently shaken for 20 sec. 100 μL of 70% ethanol was then added to each microplate well, and mixed by pipetting. The lysate was removed and applied to the wells of a RNeasy 96 (Qiagen®) plate that was placed on top of a Qiagen® Square-Well Block. The RNeasy 96 plate was sealed with tape and the Square-Well Block with the RNeasy 96 plate was loaded into the holder and placed in a rotor bucket of a 4K15C centrifuge. The sample was centrifuged at 6000 rpm (~5600×g) for 4 min at room temperature. The tape was removed from the plate and 0.8 ml of Buffer RW1 (Qiagen® RNeasy 96 kit) was added to each well of the RNeasy 96 plate. The RNeasy 96 plate was sealed with a new piece of tape and centrifuged at 6000 rpm for 4 min at room temperature. The RNeasy 96 plate was placed on top of another clean Square-Well Block, the tape removed and 0.8 ml of Buffer RPE (Qiageng® RNeasy 96 kit) was added to each well of the RNeasy 96 plate. The RNeasy 96 plate was sealed with a new piece of tape and centrifuged at 6000 rpm for 4 min at room temperature. The tape was removed and another 0.8 ml of Buffer RPE (Qiagen® RNeasy 96 kit) was added to each well of the RNeasy 96 plate. The RNeasy 96 plate was sealed with a new piece of tape and centrifuged at 6000 rpm for 10 min at room temperature. Tape was removed, the RNeasy 96 plate was placed on top of a rack containing 1.2-mL collection microtubes. The RNA was eluted by adding 50 µL of RNase-free water to each well, sealing plate with a new piece of tape and incubated for 1 min at room temperature. The plate was then centrifuged at 6000 rpm for 4 min at room temperature. The elution step was repeated with a second volume of 50 µl RNase-free water. The microtubes with total cellular RNA are stored at −70°.

Quantification of Total Cellular RNA

RNA was quantified on the STORM® system (Molecular Dynamics®) using the RiboGreen® RNA Quantification Kit (Molecular Probes®). Briefly, the RiboGreen reagent was diluted 200-fold in TE (10 mM Tris-HCl pH=7.5, 1 mM EDTA). Generally, 50 µL of reagent was diluted in 10 mL TE. A Standard Curve of ribosomal RNA was diluted in TE to 2 µg/mL and pre-determined amounts (100, 50, 40, 20, 10, 5, 2 and 0 µL) of the ribosomal RNA solution are then transferred in a new 96-well plate (COSTAR #3997) and the volume was completed to 100 µL with TE. Generally, column 1 of the 96-well plate was used for the standard curve and the other wells are used for the RNA samples to be quantified. 10 µL of each RNA sample that was to be quantified, was transferred to the corresponding well of the 96-well plate and 90 µL of TE was added. One volume (100 µL) of diluted RiboGreen reagent was added to each well of the 96-well plate and incubated for 2 to 5 minutes at room temperature, protected from light (a 10 µL RNA sample in a 200 µL final volume generates a 20×dilution). The fluorescence intensity of each well was measured on the STORM® system (Molecular Dynamics®). A standard curve was created on the basis of the known quantities of the ribosomal RNA and the resulting fluorescent intensities. The RNA concentration in the experimental samples was determined from the standard curve and corrected for the 20×dilution.

Reagents and Materials

| Product | Company | Catalog # | Storage |
|---|---|---|---|
| DEPC | Sigma | D5758 | 4° C. |
| EDTA | Sigma | E5134 | RT |
| Trizma-Base | Sigma | T8524 | RT |
| Trizma-HCl | Sigma | T7149 | RT |
| Collection Tube Strips | Qiagen | 19562 | RT |
| Ribogreen RNA Quantitation Kit | Molecular Probe | R11490 | −20° C. |
| Rneasy 96 Kit | Qiagen | 74183 | RT |
| Square-Well Blocks | Qiagen | 19573 | RT |

Real-Time RT-PCR

The Real-Time RT-PCR was performed on the ABI Prism 7700 Sequence Detection System using the TaqMan EZ RT-PCR Kit from (Perkin-Elmer Applied Biosystems®). RT-PCR was optimized for the quantification of the 5' IRES of HCV RNA by using the Taqman technology (Roche Molecular Diagnostics Systems) similar to the technique previously described (Martell et al., 1999. J. Clin. Microbiol. 37: 327–332). The system exploits the 5'-3' nucleolytic activity of AmpliTaq DNA polymerase. Briefly, the method utilizes a dual-labeled fluorogenic hybridization probe (PUTR Probe) that specifically anneals to the template between the PCR primers (primers 8125 and 7028). The 5' end of the probe contains a fluorescent reporter (6-carboxyfluorescein [FAM]) and the 3' end contains a fluorescent quencher (6-carboxytetramethylrhodamine [TAMRA]). The FAM reporter's emission spectrum was suppressed by the quencher on the intact hybridization probe. Nuclease degradation of the hybridization probe releases the reporter, resulting in an increase in fluorescence emission. The ABI Prism 7700 sequence detector measures the increase in fluorescence emission continuously during the PCR amplification such that the amplified product was directly proportion to the signal. The amplification plot was analysed early in the reaction at a point that represents the logarithmic phase of product accumulation. A point representing a defined detection threshold of the increase in the fluorescent signal associated with the exponential growth of the PCR product for the sequence detector was defined as the cycle threshold ($C_T$). $C_T$ values are inversely proportional to the quantity of input HCV RNA; such that under identical PCR conditions, the larger the starting concentration of HCV RNA, the lower the $C_T$. A standard curve was created automatically by the ABI Prism 7700 detection system by plotting the $C_T$ against each standard dilution of known HCV RNA concentration.

Reference samples for the standard curve are included on each RT-PCR plate. HCV Replicon RNA was synthesized (by T7 transcription) in vitro, purified and quantified by $OD_{260}$. Considering that 1 µg of this RNA=$2.15 \times 10^{11}$ RNA copies, dilutions are made in order to have $10^8$, $10^7$, $10^6$, $10^5$, $10^4$, $10^3$ or $10^2$ genomic RNA copies/5 µL. Total cellular Huh-7 RNA was also incorporated with each dilution (50 ng/5 µL). 5 µL of each reference standard (HCV Replicon+ Huh-7 RNA) was combined with 45 µL of Reagent Mix, and used in the Real-Time RT-PCR reaction.

The Real-Time RT-PCR reaction was set-up for the experimental samples that were purified on RNeasy 96-well plates by combining 5 µl of each total cellular RNA sample with 45 µL of Reagent Mix.

Reagents and Materials

| Product | COMPANY | Catalog # | Storage |
|---|---|---|---|
| TaqMan EZ RT-PCR Kit | PE Applied Biosystems | N808-0236 | −20° C. |
| MicroAmp Optical Caps | PE Applied Biosystems | N801-0935 | RT |
| MicroAmp Optical 96-Well Reaction Plate | PE Applied Biosystems | N801-0560 | RT |

Reagent Mix Preparation

| Component | Volume for one sample (μL) | Volume for One Plate (μL) (91 samples + Dead Volume) | Final conc. |
|---|---|---|---|
| Rnase-free water | 16.5 | 1617 | |
| 5X TaqMan EZ buffer | 10 | 980 | 1X |
| Mn(OAc)$_2$ (25 mM) | 6 | 588 | 3 mM |
| dATP (10 mM) | 1.5 | 147 | 300 μM |
| dCTP (10 mM) | 1.5 | 147 | 300 μM |
| dGTP (10 mM) | 1.5 | 147 | 300 μM |
| dUTP (20 mM) | 1.5 | 147 | 600 μM |
| Forward Primer (10 μM) | 1 | 98 | 200 nM |
| Reverse Primer (10 μM) | 1 | 98 | 200 nM |
| PUTR probe (5 μM) | 2 | 196 | 200 nM |
| rTth DNA polymerase (2.5 U/μL) | 2 | 196 | 0.1 U/μL |
| AmpErase UNG (1 U/μL) | 0.5 | 49 | 0.01 U/μL |
| Total Volume | 45 | 4410 | |

Forward Primer Sequence (SEQ ID. 1): 5'-ACG CAG AAA GCG TCT AGC CAT GGC GTT AGT-3'

Reverse Primer Sequence (SEQ ID NO. 2): 5'-TCC CGG GGC ACT CGC AAG CAC CCT ATC AGG-3'

Note: Those primers amplify a region of 256-nt present within the 5' untranslated region of HCV.

PUTR Probe Sequence (SEQ ID NO. 3):

6FAM

TGG TCT GCG GAA CCG GTG AGT ACA CC

TAMRA

No Template Controls (NTC): On each plate, 4 wells are used as "NTC". For these controls, 5 μl of water are added to the well in place of RNA.

Thermal Cycling Conditions

50° C.  2 min
60° C.  30 min
95° C.  5 min

95° C.  15 sec  } for 2 cycles
60° C.  1 min

90° C.  15 sec  } for 40 cycles
60° C.  1 min

Following the termination of the RT-PCR reaction the data analysis requires setting of threshold fluorescence signal for the PCR plate and a standard curve was constructed by plotting the Ct value versus RNA copy number used in each reference reaction. The Ct values obtained for the assay samples are used to interpolate an RNA copy number based on the standard curve.

Finally, the RNA copy number was normalized (based on the RiboGreen RNA quantification of the total RNA extracted from the cell culture well) and expressed as genome equivalents/μg of total RNA [ge/μg].

The RNA copy number [g.e./μg] from each well of the cell culture plate was a measure of the amount of replicating HCV RNA in the presence of various concentrations of inhibitor. The % inhibition was calculated with the following equation:

100−[(g.e./μg inh)/(g.e./μg ctl)×100].

A non-linear curve fit with the Hill model was applied to the inhibition-concentration data, and the 50% effective concentration ($EC_{50}$) was calculated by the use of SAS software (Statistical Software System; SAS Institute, Inc. Cary, N.C.).

When the compounds of this invention were evaluated in the preceding enzymatic and cell based assays, the compounds were found to be highly active. More specifically, the compounds had $IC_{50}$'s below 0.1 μM in the NS3-NS4A protease assay, and $EC_{50}$'s below 0.5 μM in the cell based HCV RNA replication assay.

Example 12

Specificity Assays

The specificity assays used to evaluate the selectivity of this compound are described in WO 00/09543.

When the compounds were evaluated in the specificity assays, the compounds of formula 1 were found to be selective in that they do not show significant inhibition in the Human Leukocyte Elastase and Cathepsin B assays.

Example 13

Pharmacokinetic Properties

The present compounds also show good pharmacokinetic properties such as significant plasma levels in the rat at 1 hour and 2 h after an oral dose of 5 mg/kg.

More explicitly, the following assay, an in vivo oral absorption screen, was used to determine plasma levels of test compounds in a rat after oral administration:

Materials and Methods

1. Method Used to Pool Compounds ("Cassette Selection"):
   The selection of compounds to be pooled into a "cassette" was based on their structural similarity and physicochemical properties. A solid phase extraction method applicable to all the selected compounds was established. Based on the initial testing where each compound was spiked into rat plasma and run through HPLC or HPLC/MS at a concentration of 0.5 μM, the retention time, ionic mass, and the possible separation among compounds by HPLC and/or HPLC/MS were used as basis for pooling 3–4 compounds into one "cassette".

2. Oral Vehicle and Compound Preparation:
   Each "cassette" contains 3–4 compounds at 5 or 4 mg/kg for each compound. The cassettes were prepared as an oral suspension in 0.5% aqueous methylcellulose and 0.3% of polyoxyethylene (20) sorbiton monooleate (Tween-80). The dosing volume was 10 ml/kg via oral gavage.

3. Dosing and Plasma Sampling:
   Male Sprague Dawley rats were fasted overnight in individual cages, with access to aqueous 10% dextrose. Two rats were dosed with each "cassette". Plasma samples (~1 ml) were collected at 1 and 2 h post-dosing from the 2 rats and pooled for extraction and analysis.

4. Compound Extraction and Analysis:

From each cassette, plasma samples at 1 and 2 h, blank plasma, blank plasma spiked with all the compounds at 0.5 μM of each, are extracted by the solid phase extraction method. Samples were analyzed by HPLC and HPLC/MS for comparison purpose. Plasma concentrations are estimated based on the single concentration of 0.5 μM standard.

When assayed in the preceding screen the compounds of examples 1 to 9 of this invention were found to present in significant levels in the plasma at the 1 hour and 2 hour intervals following oral administration, averaging blood plasma levels of 1.23 μM and 1.16 μM respectively. This demonstration of significant in vivo oral absorption for the compounds of this invention is unexpected, in view of the lower oral absorption generally attributed to this class of peptides. The ready oral absorption renders the compounds useful for treating of HCV infection.

The following table lists compounds representative of the invention. Further in keeping with the present disclosure, the compound all had $IC_{50}$'s below 0.1 μM in the NS3-NS4A protease assay, and $EC_{50}$'s below 0.5 μM in the cell based HCV RNA replication assay.

TABLE 1

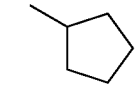

(I)

| Cpd No. | $R^1$ | $R^2$ | $R^3$ | $R^4$ | m/z $(MH)^+$ |
|---|---|---|---|---|---|
| 100 | OH | 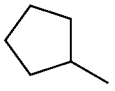 | tert-Butyl | 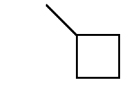 | 789.3 |
| 101 | OH | 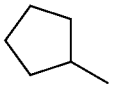 | tert-Butyl | 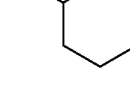 | 775.4 |
| 102 | OH | 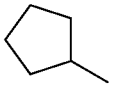 | tert-Butyl | 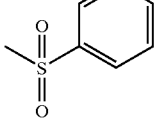 | 803.4 |
| 103 | 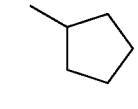 | 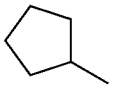 | tert-Butyl | 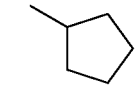 | 928.5 |
| 104 | OH | 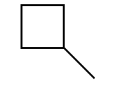 | tert-Butyl | 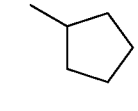 | 775.4 |
| 105 | OH | 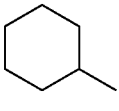 | tert-Butyl | | 803.4 |

TABLE 1-continued

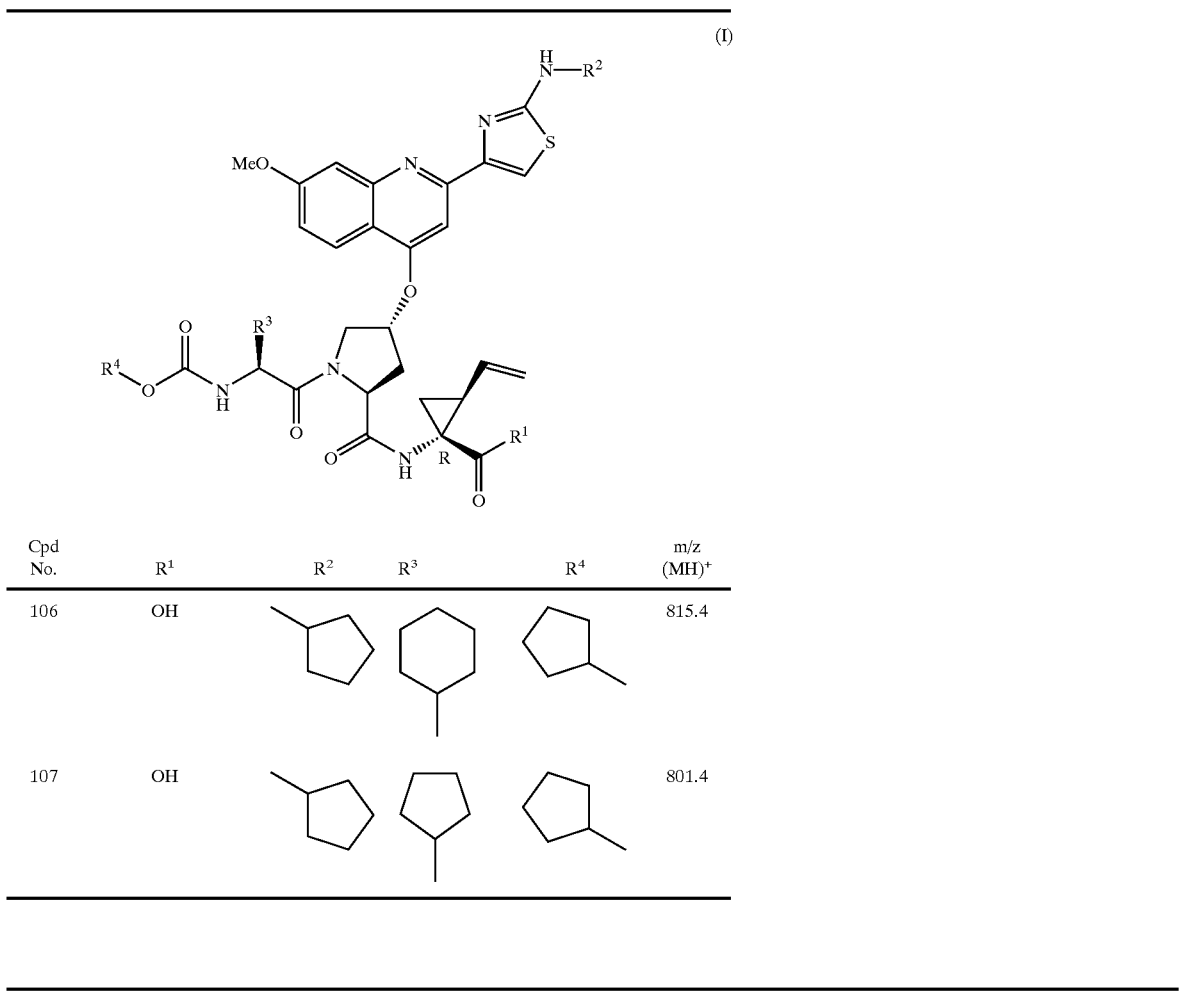

| Cpd No. | R$^1$ | R$^2$ | R$^3$ | R$^4$ | m/z (MH)$^+$ |
|---|---|---|---|---|---|
| 106 | OH | cyclopentyl | cyclohexyl | cyclopentylmethyl | 815.4 |
| 107 | OH | cyclopentyl | cyclopentyl | cyclopentylmethyl | 801.4 |

What is claimed is:

1. A compound of formula (I):

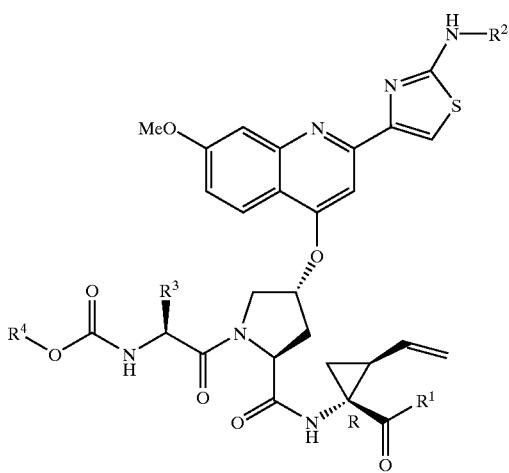

wherein $R^1$ is hydroxy or $NHSO_2R^{1A}$ wherein $R^{1A}$ is $(C_{1-8})$alkyl, $(C_{3-7})$cycloalkyl or $\{(C_{1-6})$alkyl-$(C_{3-7})$cycloalkyl$\}$, which are all optionally substituted from 1 to 3 times with halo, cyano, nitro, $O$—$(C_{1-6})$alkyl, amido, amino or phenyl, or $R^{1A}$ is $C_6$ or $C_{10}$ aryl which is optionally substituted from 1 to 3 times with halo, cyano, nitro, $(C_{1-6})$alkyl, $O$—$(C_{1-6})$alkyl, amido, amino or phenyl; $R^2$ is $(C_{4-6})$cycloalkyl; $R^3$ is t-butyl or $(C_{5-6})$ cycloalkyl and $R^4$ is $(C_{4-6})$cycloalkyl; or a pharmaceutically acceptable salt thereof.

2. The compound of formula I according to claim 1, wherein $R^1$ is hydroxy, $NHSO_2Me$, $NHSO_2$cyclopropyl or $NHSO_2Ph$.

3. The compound of formula I according to claim 2, wherein $R^1$ is $NHSO_2$cyclopropyl or $NHSO_2Ph$.

4. The compound of formula I according to claim 2, wherein $R^1$ is hydroxy.

5. The compound of formula I according to claim 1, wherein $R^2$ is cyclopentyl or cyclohexyl.

6. The compound of formula I according to claim 5, wherein $R^2$ is cyclopentyl.

7. The compound of formula I according to claim 1, wherein $R^3$ is t-butyl or cyclohexyl.

8. The compound of formula I according to claim 7, wherein $R^3$ is t-butyl.

9. The compound of formula I according to claim 1, wherein $R^4$ is cyclobutyl or cyclopentyl.

10. The compound of formula I according to claim 9, wherein $R^4$ is cyclopentyl.

11. The compound of formula I according to claim 1, wherein $R^1$ is hydroxy, $R^2$ and $R^4$ each is cyclopentyl and $R^3$ is t-butyl.

12. The compound of formula I according to claim 1, wherein $R^1$ is hydroxy, $R^2$ is cyclobutyl, $R^3$ is t-butyl and $R^4$ is cyclopentyl.

13. The compound of formula I according to claim 1, wherein $R^1$ is hydroxy, $R^2$ is cyclohexyl, $R^3$ is t-butyl and $R^4$ is cyclopentyl.

14. The compound of formula I according to claim 1, wherein $R^1$ is $NHSO_2Ph$, $R^2$ and $R^4$ each is cyclopentyl and $R^3$ is t-butyl.

15. The compound of formula I according to claim 1, wherein $R^1$ is hydroxy, $R^2$ is cyclopentyl, $R^3$ is t-butyl and $R^4$ is cyclobutyl.

16. The compound of formula I according to claim 1, wherein $R^1$ is hydroxy, $R^2$ is cyclopentyl, $R^3$ is t-butyl and $R^4$ is cyclohexyl.

17. The compound of formula I according to claim 1, wherein $R^1$ is hydroxy, $R^2$ and $R^4$ each is cyclopentyl and $R^3$ is cyclohexyl.

18. The compound of formula I according to claim 1, wherein $R^1$ is hydroxy, $R^2$, $R^3$ and $R^4$ each is cyclopentyl.

19. A pharmaceutical composition comprising an anti-hepatitis C virally effective amount of a compound of formula I according to claim 1, or a pharmaceutically acceptable salt thereof, in admixture with one or more pharmaceutically acceptable carriers, adjuvants or vehicles.

20. The pharmaceutical composition according to claim 19, further comprising one or more other anti-HCV agents.

21. The pharmaceutical composition according to claim 20, wherein at least one of the other anti-HCV agents is selected from: α-interferon or pegylated α-interferon.

22. The pharmaceutical composition according to claim 20, wherein at least one of the other anti-HCV agents is ribavirin.

23. The pharmaceutical composition according to claim 20, wherein at least one of the other anti-HCV agents is an HCV polymerase inhibitor.

24. The pharmaceutical composition according to claim 20, wherein at least one of the other anti-HCV agents is selected from inhibitors of: helicase, NS2/3 protease and internal ribosome entry site (IRES).

25. A method for treating a hepatitis C viral infection in a mammal comprising administering to the mammal an anti-hepatitis C virally effective amount of a compound of formula I according to claim 1, or a pharmaceutically acceptable salt thereof.

26. A method for treating a hepatitis C viral infection in a mammal comprising administering to the mammal an anti-hepatitis C virally effective amount of the composition according to claim 19.

27. A method for treating a hepatitis C viral infection in a mammal comprising administering to the mammal an anti-hepatitis C virally effective amount of the composition according to claim 20.

28. A method for treating a hepatitis C viral infection in a mammal comprising administering to the mammal an anti-hepatitis C virally effective amount of a combination of the compound of formula I according to claim 1, or a pharmaceutically acceptable salt thereof, and one or more other anti-HCV agents, wherein said one or more other anti-HCV agents are administered prior to, concurrently with, or following the administration of the compound of formula I according to claim 1, or a pharmaceutically acceptable salt thereof.

29. The method according to claim 28, wherein at least one of the other anti-HCV agents is selected from: α-interferon or pegylated α-interferon.

30. The method according to claim 28, wherein at least one of the other anti-HCV agents is ribavirin.

31. The method according to claim 29, wherein at least one of the other anti-HCV agents is ribavirin.

32. The method according to claim 28, wherein at least one of the other anti-HCV agents is an inhibitor of HCV polymerase.

33. The method according to claim 28, wherein at least one of the other anti-HCV agents is selected from inhibitors of: helicase, NS2/3 protease and internal ribosome entry site (IRES).

34. The method according to claim 29, wherein at least one of the other anti-HCV agents is selected from inhibitors of: helicase, NS2/3 protease and internal ribosome entry site (IRES).

35. The method according to claim 30, wherein at least one of the other anti-HCV agents is selected from inhibitors of: helicase, NS2/3 protease and internal ribosome entry site (IRES).

36. The method according to claim 31, wherein at least one of the other anti-HCV agents is selected from inhibitors of: helicase, NS2/3 protease and internal ribosome entry site (IRES).

* * * * *

UNITED STATES PATENT AND TRADEMARK OFFICE
CERTIFICATE OF CORRECTION

PATENT NO. : 6,642,204 B2  
APPLICATION NO. : 10/353589  
DATED : November 4, 2003  
INVENTOR(S) : Montse Llinas-Brunet and Vida J. Gorys It is certified that error appears in the above-identified patent and that said Letters Patent is hereby corrected as shown below:

In the Abstract, delete the chemical structure of formula (1) and replace with the following chemical structure:

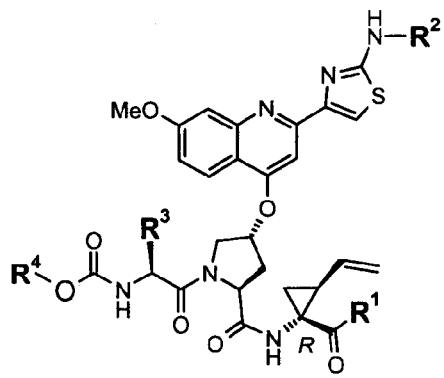

In column 22, line 30, delete the chemical structure above the arrow and replace with the following chemical structure:

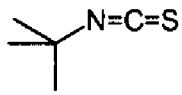

In column 23, lines 3 and 20, delete the chemical structure above the arrow and replace with the following chemical structure:

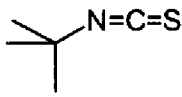

In column 23, lines 61 and 62, delete "N-benzyloxy-N'-cyclopropyl thiourea" and insert --N-benzoyl-N'-cyclopropyl thiourea--.

UNITED STATES PATENT AND TRADEMARK OFFICE
CERTIFICATE OF CORRECTION

PATENT NO. : 6,642,204 B2
APPLICATION NO. : 10/353589
DATED : November 4, 2003
INVENTOR(S) : Montse Llinas-Brunet and Vida J. Gorys It is certified that error appears in the above-identified patent and that said Letters Patent is hereby corrected as shown below:

In column 48, in Table 1, in the entry for Compound No. 103, delete the chemical structure " 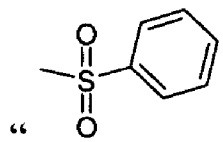 " and insert the following chemical structure:

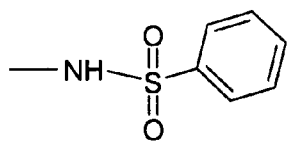

Signed and Sealed this

Eleventh Day of July, 2006

JON W. DUDAS
*Director of the United States Patent and Trademark Office*